(12) United States Patent
Staab et al.

(10) Patent No.: US 12,310,897 B2
(45) Date of Patent: May 27, 2025

(54) NEGATIVE PRESSURE AEROSOLIZATION MITIGATION DEVICES AND METHODS

(71) Applicant: The University of Kansas, Lawrence, KS (US)

(72) Inventors: Jared Staab, Lenexa, KS (US); Brent Barta, Malcom, NE (US); Brigid Flynn, Leawood, KS (US); Tim Krause, Stilwell, KS (US); Jay Nachtigal, Leawood, KS (US)

(73) Assignee: THE UNIVERSITY OF KANSAS, Lawrence, KS (US)

( * ) Notice: Subject to any disclaimer, the term of this patent is extended or adjusted under 35 U.S.C. 154(b) by 897 days.

(21) Appl. No.: 17/219,330

(22) Filed: Mar. 31, 2021

(65) Prior Publication Data

US 2021/0307985 A1    Oct. 7, 2021

Related U.S. Application Data

(60) Provisional application No. 63/004,944, filed on Apr. 3, 2020.

(51) Int. Cl.
*A61G 10/00* (2006.01)
*A61G 10/02* (2006.01)

(52) U.S. Cl.
CPC .......... *A61G 10/005* (2013.01); *A61G 10/02* (2013.01)

(58) Field of Classification Search
CPC .......... A61F 13/10; A61F 13/60; A61F 13/82; A61F 2013/00846; A61B 46/27;
(Continued)

(56) References Cited

U.S. PATENT DOCUMENTS 3,000,379 A    9/1961   Viers
6,217,507 B1 *  4/2001   Bonvik ............... A61G 10/005
                                                600/21
(Continued)

FOREIGN PATENT DOCUMENTS

CN    2841852 Y    11/2006
EP    3542658 A1    9/2010
(Continued)

OTHER PUBLICATIONS

Scone Medical Solutions; Scone Device; https://www.sconemed.com/scone-device; 12 pages; last accessed Jun. 30, 2021.
(Continued)

*Primary Examiner* — Ophelia A Hawthorne
*Assistant Examiner* — Michael Milo
(74) *Attorney, Agent, or Firm* — Jake M. Gipson; Bradley Arant Boult Cummings LLP

(57) ABSTRACT

An aerosolization mitigation device is provided. The aerosolization mitigation device can include a negative pressure aerosolization mitigation system. A transparent barrier can form a frame of the system, and a negative pressure can be generated in the internal volume. The device can isolate a patient to allow ambulatory, surgical, and routine care to proceed during periods of higher patient volume or viral transmission. The negative pressure environment mitigates viral transmission to protect healthcare providers and others in the vicinity of the patient from health risks during patient care.

14 Claims, 26 Drawing Sheets

(58) Field of Classification Search
CPC ... A61B 2046/205; A61B 46/00; A61B 46/20;
A61B 46/40; A61B 90/05; A61G 13/10;
A61G 13/12; A61G 13/1235; A61G
13/124; A61G 10/005; A61G 10/02;
A61L 31/00
USPC .... 602/20, 21, 63, 60, 75, 61, 3, 42, 62, 43,
602/41; 128/851, 855, 856, 854, 853,
128/849, 878, 877, 846; 607/104, 114,
607/107; 165/46
See application file for complete search history.

(56) References Cited

U.S. PATENT DOCUMENTS

| | | | |
|---|---|---|---|
| 6,461,290 B1 | 10/2002 | Reichman et al. | |
| 6,899,668 B2 | 5/2005 | Paranjpe | |
| 7,037,254 B2 | 5/2006 | O'Connor et al. | |
| 7,503,890 B2 | 3/2009 | Kubicsko et al. | |
| 7,757,689 B2 | 7/2010 | Chang | |
| 10,363,113 B1* | 7/2019 | Chenger | A61B 50/30 |
| 2002/0112754 A1 | 8/2002 | Gauger et al. | |
| 2005/0261615 A1 | 11/2005 | Weston | |
| 2006/0247487 A1* | 11/2006 | Arts | A61G 11/009 600/21 |
| 2015/0238264 A1* | 8/2015 | Kerns | A61B 46/23 128/852 |
| 2016/0166455 A1 | 6/2016 | Steinert | |
| 2017/0340407 A1* | 11/2017 | Ahrens | A61B 17/3423 |
| 2017/0340846 A1* | 11/2017 | Gramann | A61M 11/06 |
| 2019/0380901 A1 | 12/2019 | Breegi | |
| 2021/0322244 A1* | 10/2021 | Moore | E04H 15/20 |

FOREIGN PATENT DOCUMENTS

| | | |
|---|---|---|
| JP | 2004344320 A | 12/2004 |
| WO | 2018/144809 A1 | 8/2018 |

OTHER PUBLICATIONS

RADM Denise M. Hinton, Chief Scientist, Food and Drug Administration; https://www.fda.gov/media/139391/download; 7 pages; last accessed Jun. 30, 2021.

Stat Enclosure; Olifant Medical; Procedural Safety Hood Designed to Mitigate Droplet and Aerosol Exposure !; https://www.olifantmedical.com/statenclosure; 2 pages; last accessed Jun. 30, 2021.

Instructions for Healthcare Provider (HCP): Use of the Airway Dome; https://www.fda.gov/media/140454/download; 15 pages; last accessed Jun. 30, 2021.

Nurse Saver, NRSAVR-100; https://www.intubationhood.com/; 4 pages; last accessed Jun. 30, 2021.

EpiGuard; Medical isolation and transportation systems; https://epiguard.com/products/; 40 pages; last accessed Jun. 30, 2021.

Bassin et al.; "Rapid development of a portable negative pressure procedural tent"; Apr. 29, 2020; https://theunion.org/sites/default/files/2020-09/IJTLD-0317_Letter-Bassin_0.pdf; 6 pages; last accessed Jun. 30, 2021.

Carnett; "Pandemic inspires health-tech innovation as businesses strive for safety"; Nonprofit journalism for an informed community; Aug. 13, 2020; https://sanantonioreport.org/pandemic-inspires-health-tech-innovation-as-businesses-strive-for-safety/; 9 pages; last accessed Jun. 30, 2021.

Mead et al.; "NIOSH Ventilated Headboard Provides Solution to Patient Isolation During an Epidemic"; Apr. 14, 2020; https://blogs.cdc.gov/niosh-science-blog/2020/04/14/ventilated-headboard/; 5 pages; last accessed Jul. 1, 2021.

Rajajee et al.; "Use of a Novel Negative-Pressure Tent During Bedside Tracheostomy in COVID-19 Patients"; Aug. 7, 2020; https://www.ncbi.nlm.nih.gov/pmc/articles/PMC7413643/; 12 pages; last accessed Jul. 1, 2021.

International Search Report and Written Opinion of the International Searching Authority issued in PCT/US2021/025160, mailed Jul. 1, 2021, 16 pages.

Office action for JP Pat. App. No. 2022-558412 issued Nov. 21, 2024, and a machine English translation thereof.

* cited by examiner

Negative pressure aerosolization mitigation box
Side View

Clear acrylic box of various sizes(larger for extubation in the ICU. Smaller for code blue situation, small pediatric version) 3000

Adhesive drape-conforms to floor, patient and bed seat off from external environment 3220

Self Sealing access ports for healthcare personnel or equipment 3500

Suction port to wall or portable suction 3400

FIG. 17

NEGATIVE PRESSURE AEROSOLIZATION MITIGATION DEVICES AND METHODS

CROSS REFERENCE TO RELATED APPLICATIONS

The present application claims benefit of and priority to U.S. Provisional Patent App. No. 63/004,944, filed Apr. 3, 2020, and is incorporated herein by reference in its entirety for all purposes.

FIELD

The present disclosure relates to disease transmission mitigation. In particular, embodiments relate to negative pressure aerosolization mitigation, including a single person system.

BACKGROUND

In the course of patient care, healthcare providers can be vulnerable to respiratory infections from aerosolization and droplet transmission of pathogens discharged by patients requiring care. Often, treatment requires providers to be in close proximity to patients for prolonged periods of time, exposing them to health risks. Additionally, in situations such as pandemics, the volume of patient care is significantly increased such that providers are more often in the vicinity of patients suffering from diseases. Environments in which care is provided also experience increased use and high patient turnover, which support the spread of communicable diseases because pathogens carrying diseases can both contaminate surfaces and be suspended in the air for long periods of time. Without any respite from patient care, these rooms can compound the spread of communicable diseases and further expose providers to significant health risks.

Personal protective equipment (PPE) can be worn to mitigate transmission, however, PPE does not prevent transmission to personnel who are not wearing PPE. Especially during periods where the volume of patient care is increased, PPE can be difficult to source. PPE shortages leaves vulnerable those who are needed and present for patient care, but cannot be provided with new or adequate PPE. PPE also does not prevent contamination of surfaces. Thus, anyone proximate to surfaces in a patient care environment is vulnerable to disease, especially if sufficient PPE is not available. Without proper cleaning of surfaces, the contamination can last for days and significantly increase the risk of transmission.

Disease transmission mitigation is therefore important to achieve in alternative ways to reduce the dependency on PPE and provide needed protection. Generating negative pressure in patient care environments can help to prevent transmission of infectious diseases. In combination with PPE, transmission can be significantly reduced. Devices and methods described herein utilize negative pressure aerosolization mitigation ("NPAM") to protect those proximate to patients with communicable diseases by containing patients in a confined negative pressure environment, thereby further reducing or eliminating aerosolization and droplet transmission.

BRIEF SUMMARY

In some embodiments, an aerosolization mitigation device can include an inflatable strut system, and a transparent barrier configured to enclose a portion of a patient in a contained environment. The transparent barrier can form a volume around the patient when the inflatable strut system is in an inflated state, and the aerosolization mitigation device can include an opening configured to be sealed around the patient, a negative pressure channel configured to be coupled to a source of negative pressure, and an access port configured to provide a flow limited passageway through the transparent barrier into the volume around the patient when the inflatable strut system is in an inflated state. The negative pressure can be generated in the volume around the patient in response to the application of the source of negative pressure.

In some embodiments, the inflatable strut system can include inflatable tubing forming a commonly inflatable volume, and an inflation port. The inflation port can be fluidically coupled to the inflatable strut system.

In some embodiments, the inflatable tubing can form a generally rectangular outline of a large and unobstructed view of the contained environment.

In some embodiments, the opening can include a drape that extends outwardly from the transparent barrier. In some embodiments, the transparent barrier includes the opening. The transparent barrier can further include a frame configured to enclose at least a head of the patient, and a drape configured to seal the opening around at least a portion of a neck of the patient. The frame and the drape can be sealed together at the opening such that fluid communication between the volume around the patient and an environment external to the transparent barrier is prevented.

In some embodiments, the frame can include a first material, and the drape can include a second material different than the first material. The first material can be less flexible than the second material. In some embodiments, a front edge of the neck drape can further include a closing mechanism configured to close around the patient to maintain the negative pressure in the volume around the patient. The closing mechanism can include at least one of a string, adhesive, or elastic.

In some embodiments, the transparent barrier can further include a plurality of wall panels configured to seal with the inflatable strut system to prevent fluid communication between the volume around the patient and an environment external to the transparent barrier. In some embodiments, one of the plurality of wall panels on a side of the transparent barrier can be configured to form an acute angle with a longitudinal axis generally perpendicular to a flat plane on which the aerosolization mitigation device is positioned in the inflated state. In some embodiments, two of the plurality of wall panels positioned at a rear side of the transparent barrier can be at an obtuse angle relative to each other in the inflated state. In some embodiments, the flow limited passageway can include a breakable seal that extends across the access port and is pierced to access the volume around the patient. In some embodiments, the aerosolization mitigation device can further include an attachment disposed on the transparent barrier to support at least one of a tool or an electronic device.

In some embodiments, the aerosolization mitigation device can include a negative pressure relief valve disposed on the transparent barrier to provide an indication of a positive pressure event or a high negative pressure event in the volume around the patient.

In some embodiments, the aerosolization mitigation device can include a negative pressure flow gauge corresponding to one or more markings formed on the transparent barrier.

In some embodiments, a method of deploying a personal aerosolization mitigation device can include inflating an inflatable strut system of the personal aerosolization mitigation device; positioning a patient's head within a volume of the personal aerosolization mitigation device through an opening in the inflatable strut system, the volume formed from a transparent barrier supported by the inflatable strut system; coupling a negative pressure channel of the personal aerosolization mitigation device to a source of negative pressure; and verifying, via a pressure measurement, that the pressure generated in the volume of the personal aerosolization mitigation device is lower than an ambient pressure of an external environment.

In some embodiments, the method of deploying a personal aerosolization mitigation device can further include verifying, via a pressure measurement of the inflatable strut system, that the inflatable strut system is sufficiently inflated. In some embodiments, the method of deploying a personal aerosolization mitigation device can further include closing the opening of the inflatable strut system such that the patient's head is enclosed within the volume of the personal aerosolization mitigation device and fluid communication between the volume of the personal aerosolization mitigation device and the external environment is prevented.

In some embodiments, the method of deploying a personal aerosolization mitigation device can further include positioning in the volume of the personal aerosolization mitigation device at least one of an instrument, tool, or electronic device. In some embodiments, the method of deploying a personal aerosolization mitigation device can further include monitoring the oxygen saturation in the volume of the personal aerosolization mitigation device to determine if oxygen is to be introduced into the volume of the personal aerosolization mitigation device. In some embodiments, the method of deploying a personal aerosolization mitigation device can further include oxygenating the volume of the personal aerosolization mitigation device by introducing oxygen into the volume while maintaining the pressure generated in the volume of the personal aerosolization mitigation device.

In some embodiments, a personal aerosolization mitigation device can include a foldable structure. The foldable structure can include a transparent barrier configured to enclose a patient's head in a sealed environment, where the transparent barrier forms a volume around the patient when the structure is in an assembled state; a rod coupled to a top and a bottom of the transparent barrier and configured to maintain a fixed shape of the transparent barrier when the foldable structure is in the assembled state; a negative pressure channel configured to be coupled to a source of negative pressure, wherein the volume formed around the patient maintains a pressure that is lower than an ambient pressure of the external environment; and an access port configured to provide a flow limited passageway through the transparent barrier into the volume around the patient when the foldable structure is in the assembled state. The rod can be foldable such that to deploy the foldable structure to the assembled state, the rod is extended. In some embodiments, the transparent barrier can include an opening to receive the patient. In some embodiments, the personal aerosolization mitigation device can further include a plurality of foldable rods. The foldable structure can be rapidly deployed to the assembled state by simultaneously extending the plurality of rods.

BRIEF DESCRIPTION OF THE DRAWINGS/FIGURES

The accompanying drawings, which are incorporated herein and form part of the specification, illustrate embodiments and, together with the description, further serve to explain the principles of the embodiments and to enable a person skilled in the relevant art(s) to make and use the embodiments.

Figure 14:
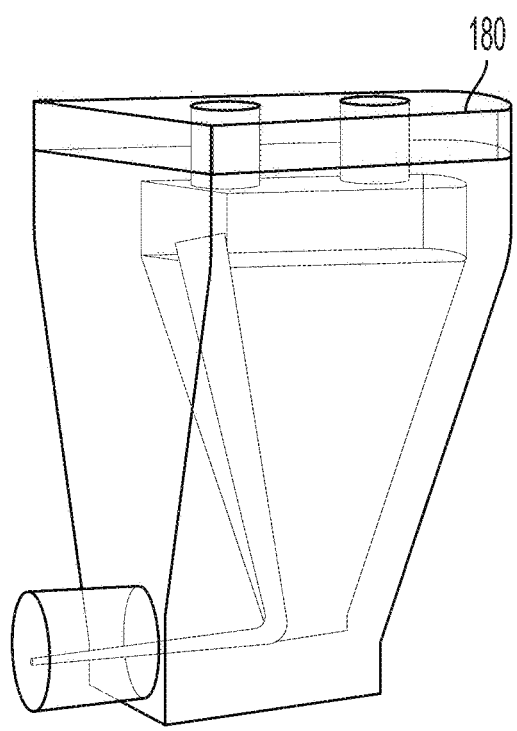

FIG. 14 a perspective cross-sectional view of a negative pressure flow gauge according to an embodiment.

Figure 15:
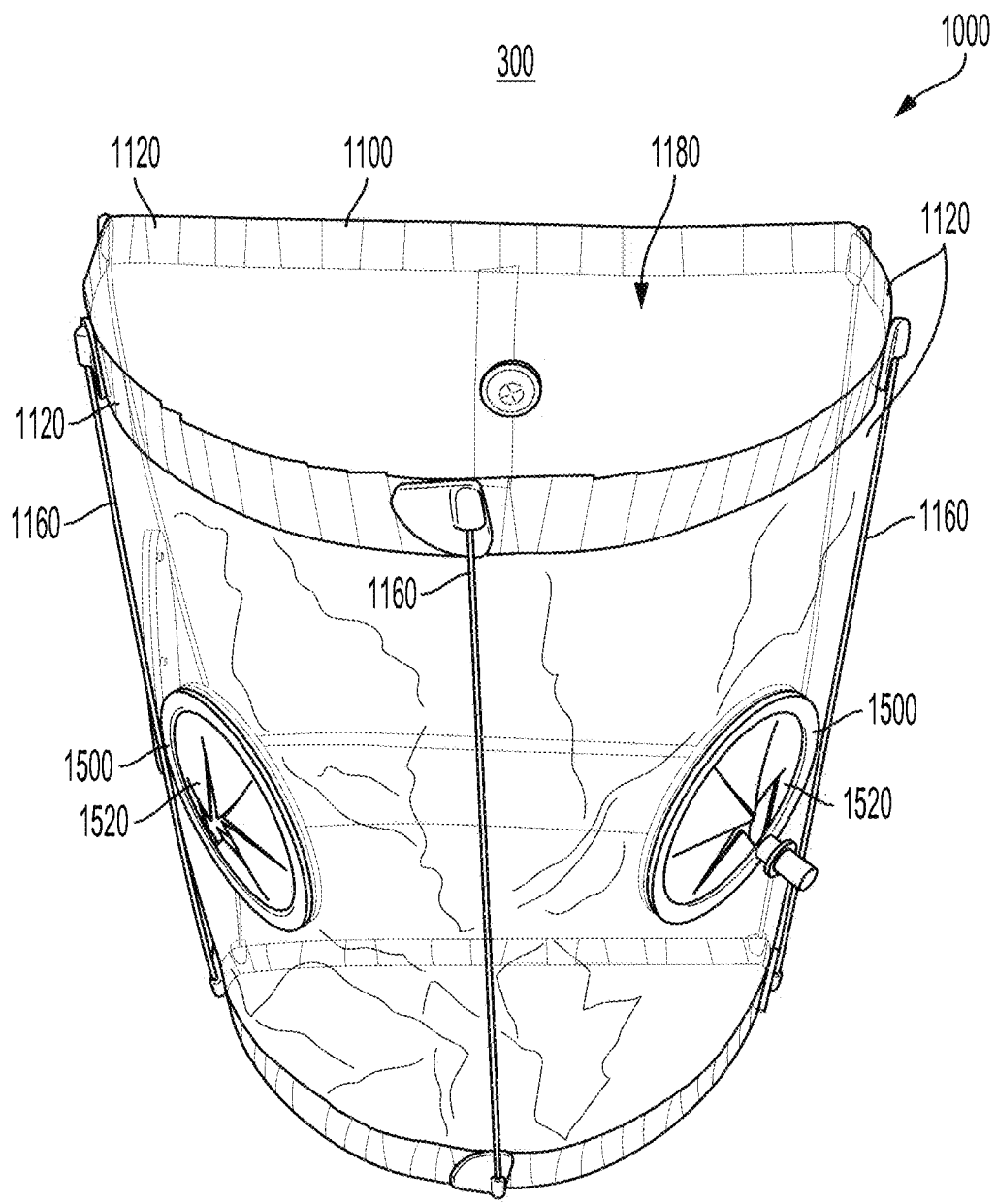

FIG. 15 is a perspective view of a rigid NPAM device according to an embodiment.

Figure 16A:
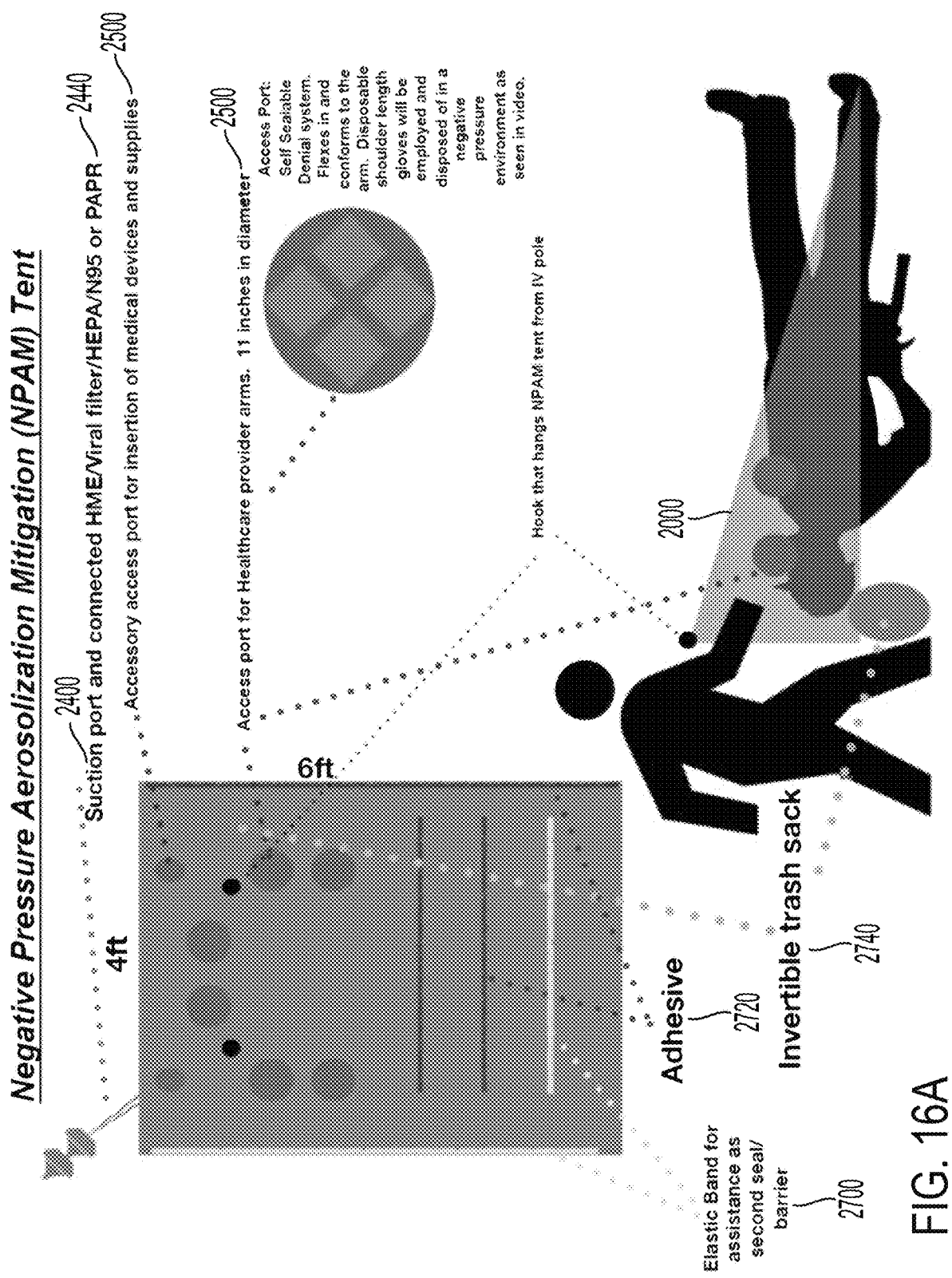

FIG. 16A is a schematic of a tent NPAM device according to an embodiment.

Figure 16B:
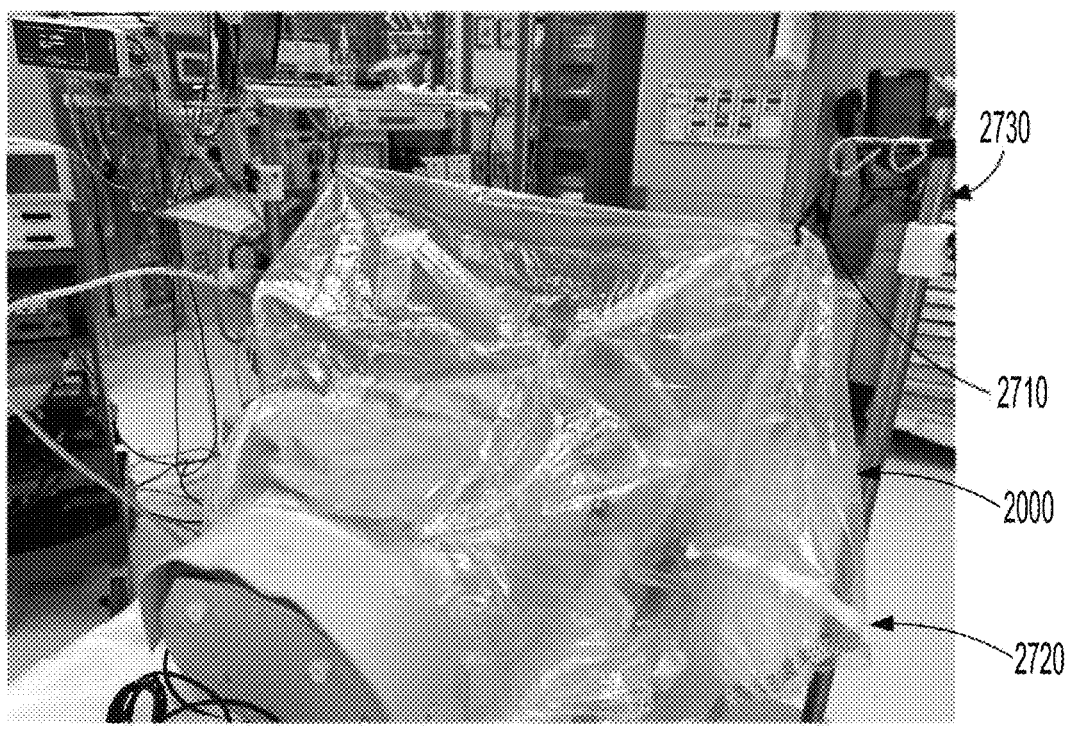

FIG. 16B is a perspective view of the tent NPAM device of FIG. 16A.

Figure 16C:

FIG. 16C is a perspective view of the tent NPAM device of FIG. 16A.

Figure 16D:

FIG. 16D is a perspective view of the tent NPAM device of FIG. 16A.

Figure 16E:

FIG. 16E is a perspective view of the tent NPAM device of FIG. 16A.

Figure 16F:

FIG. 16F is a perspective view of the tent NPAM device of FIG. 16A.

FIG. 17 is a schematic of a rigid box NPAM device according to an embodiment.

Figure 18:
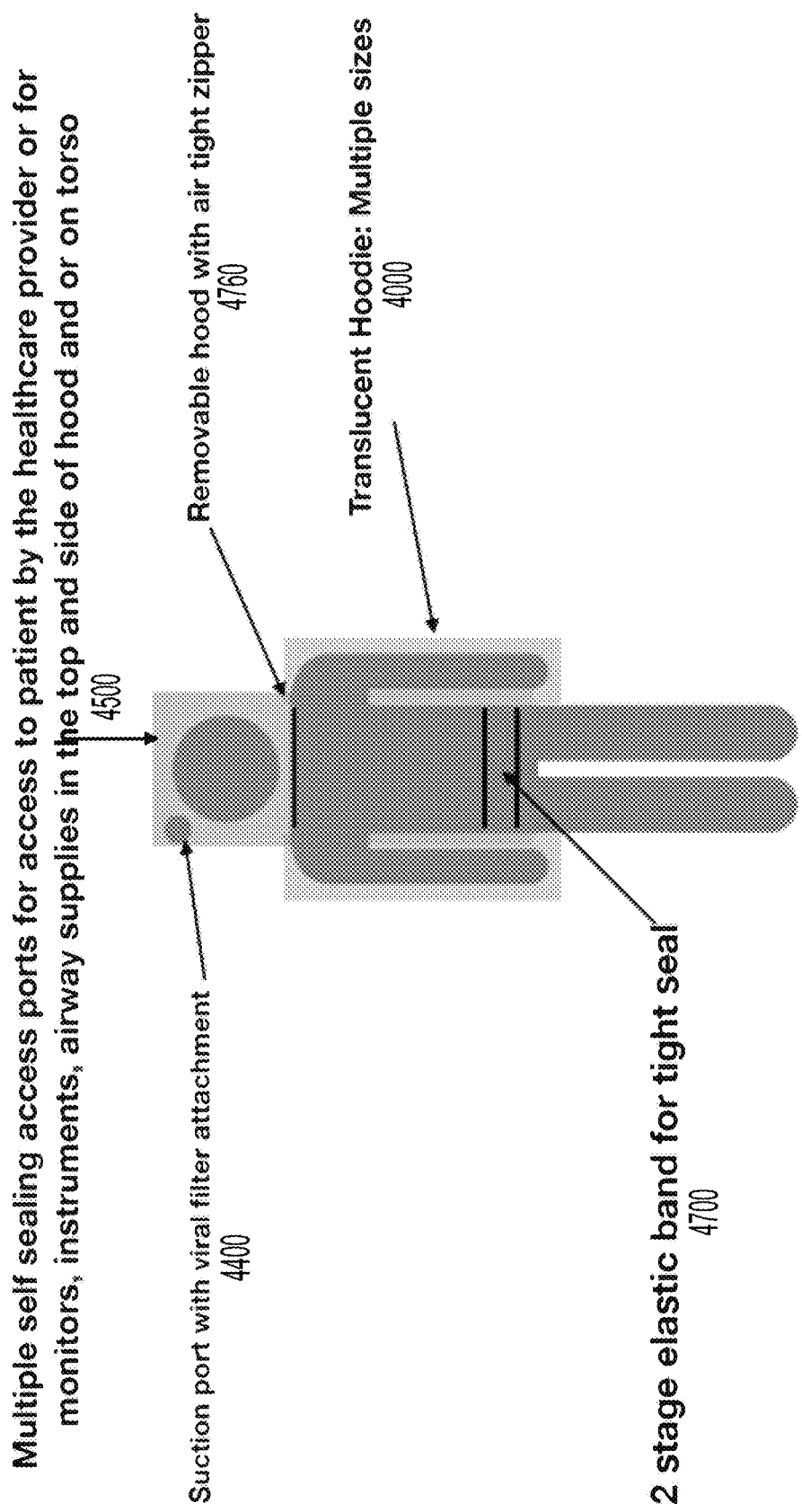

FIG. 18 is a schematic of a wearable NPAM device according to an embodiment.

Figure 19A:
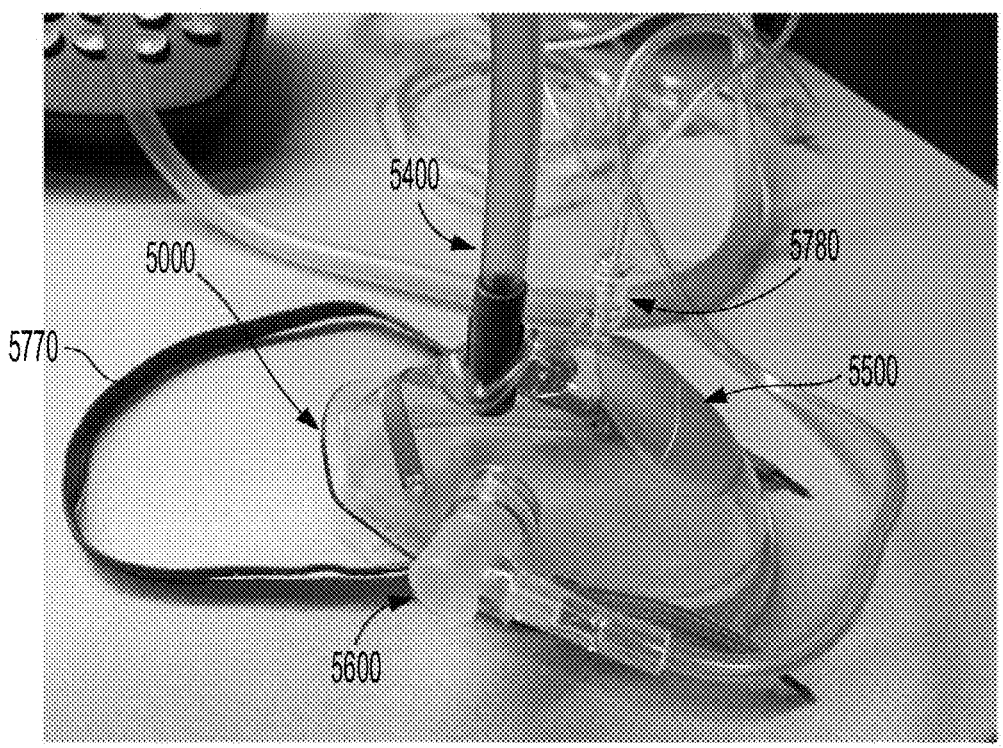

FIG. 19A is a perspective view of a mask NPAM device according to an embodiment.

Figure 19B:
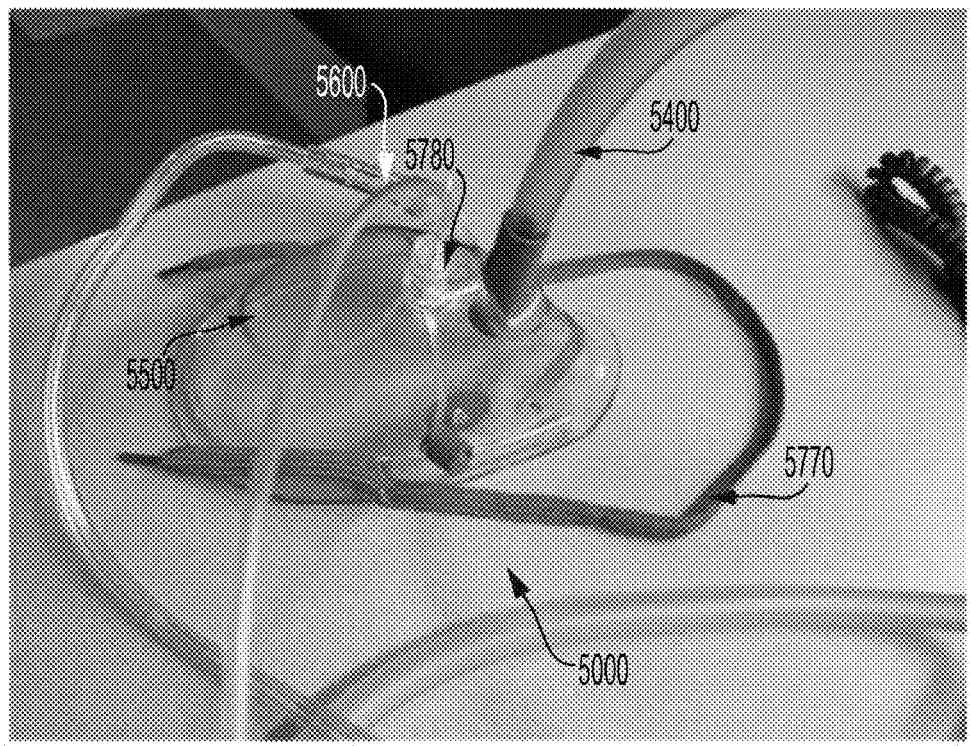

FIG. 19B is a perspective view of the mask NPAM device of FIG. 19A.

Figure 19C:
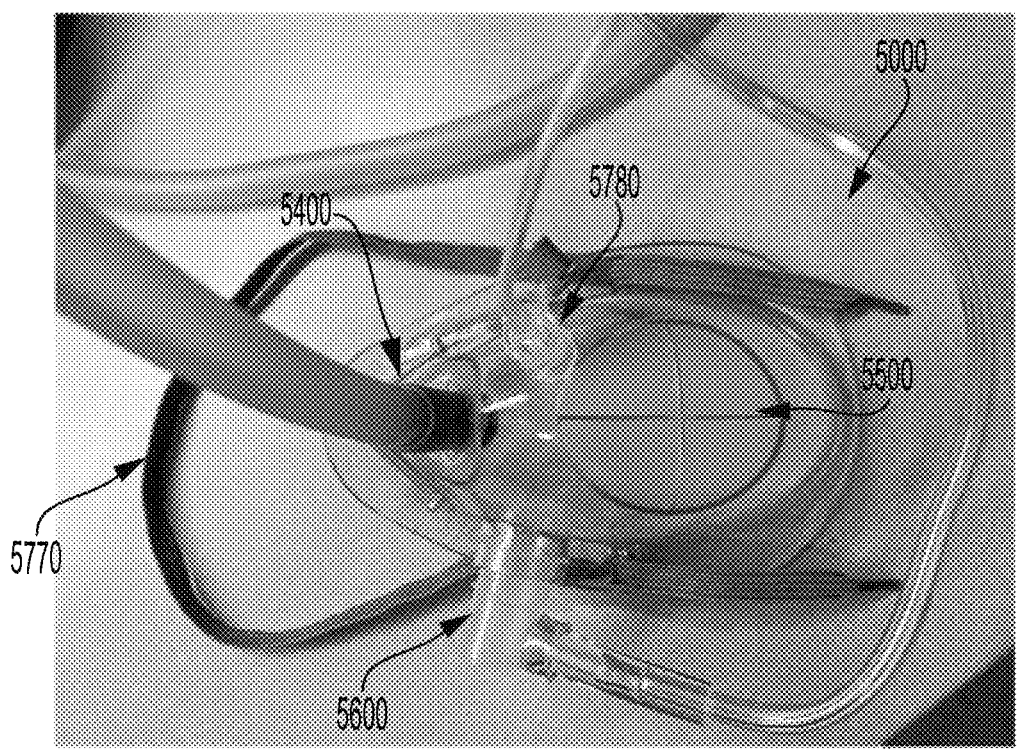

FIG. 19C is a perspective view of the mask NPAM device of FIG. 19A.

The features and advantages of the embodiments will become more apparent from the detail description set forth below when taken in conjunction with the drawings, in which like reference characters identify corresponding elements throughout. In the drawings like reference numbers generally indicate identical, functionally similar, and/or structurally similar elements.

DETAILED DESCRIPTION

The present invention(s) will now be described in detail with reference to embodiments thereof as illustrated in the accompanying drawings. References to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following examples are illustrative, but not limiting, of the present embodiments. Other suitable modifications and adaptations of the variety of conditions and parameters normally encountered in the field, and which would be apparent to those skilled in the art, are within the spirit and scope of the disclosure.

As used herein, the term "approximately" is inclusive of the number to which it refers and includes numbers that bound and are within a range of 10-15% except where such number would exceed 100% of a possible value.

As discussed above, healthcare workers take many precautions to prevent being infected by a patient with a respiratory infection, frequently by using PPE. Aerosolization and droplet spread of pathogens accounts for transmission to people providing assistance in forms of airway management, invasive diagnostic or therapeutic procedure and other necessary elements of patient care. Additionally, aerosolized and droplets eventually settle and contaminate surfaces, sometimes for days, compounding the spread. Healthcare providers and first responders can be in harm's way while treating people with communicable diseases.

Embodiments provide NPAM devices and methods. The embodiments described herein can provide a novel negative pressure environment with pathogen filtration to mitigate aerosolization and droplet transmission. The negative pressure environment can contain a patient (or portions of a patient) or multiple patients (or portions of multiple patients) who discharge biological contaminants. This helps to protect providers and others in the vicinity of a patient or a pathogen pathway, including those who are especially susceptible to both airborne transmission and contaminated surfaces. NPAM devices and methods implementing the negative pressure environment reduce the risk of aerosolization and droplet transmission thereby providing a safer environment during patient care for those proximate to the patient and/or the pathogen pathway.

Disease transmission is compounded by epidemics and pandemics, which can grow rapidly and further place those in healthcare environments at risk. Rapid growth can be attributed, in part, to novel and emerging pathogens that can spread without past exposure and, therefore, without immunological memory. The COVID-19, H1N1 (1918; 2009), H2N2 (1958), and H3N2 (1968) viral outbreaks demonstrate the devastating effects of rapid transmission. Aerosolization and droplet transmission can particularly reach providers performing various necessary elements of patient care, such as airway management, invasive diagnostics, and therapeutic procedures. While the above are notable viral pandemics, diseases caused by aerosolization of viral and bacterial pathogens are even more common than reported. Viral particles can remain airborne for 30 minutes or longer, and surfaces in the pathogen pathway can additionally become contaminated for days, which can compound the viral spread. Accordingly, healthcare providers, personnel, and first responders are commonly at risk of exposure while treating people with communicable diseases.

Reducing the harmful spread of viral particles can contain epidemics and pandemics, which can reduce the risk of exposure to healthcare providers and first responders. In addition, containing viral spread can reduce stress on infrastructure and supplies as high volume of patient care and transmission of disease can aggravate both resources. To protect providers and reduce transmission, PPE can be used, such as N95 face masks, surgical gowns, mask filters, face shields, and goggles. However, PPE shortages can result, and cannot protect others who do not have access to sufficient PPE, such as if the supply is diminished. Additionally, PPE does not prevent proximate surfaces from being contaminated. It is also beneficial to conserve PPE and reduce individual PPE requirements. Powered Air-Purifying Respirators (PAPR) are useful for aerosol-generating procedures, but have the same limitations as PPE and additionally can be cumbersome to use. Infection control using the NPAM device can decrease the need for PPE use (PAPR and N95 masks) for the providers caring for the patient, offering financial and environmental benefits. Containing possible pathogens in an enclosed negative pressure environment can potentially lead to decreased time for cleaning after a procedure, which decreases room turnover cost, saves time and labor by avoiding terminal cleaning, allowing for increased throughput through the operating room (OR), wards, or intensive care unit (ICU).

The NPAM device described herein (also can be referred to as a "negative pressure device" or "aerosolization mitigation device") can enclose a patient (or patients) at least partially in a negative pressure environment. The device can be useful in enabling triage and emergent critical care procedures. Additionally, the device can allow for numerous procedures, such as endotracheal intubation and extubation, bronchoscopy, hemodynamic monitoring invasive catheterization, esophagogastroduodenoscopy (EGD), transesophageal echocardiography (TEE), procedures involving the ear, nose, and throat, and Advanced Cardiovascular Life Support (ACLS), including chest compressions, all while mitigating the risk of aerosolization and droplet transmission to providers in the vicinity of the patient. During a pandemic, elective and some non-elective surgeries or procedures can be canceled due to limited resources and risk of possible contamination. The device can allow low risk patients to proceed with undergoing elective and non-elective surgeries or procedures. For example, a low risk and asymptomatic patient can arrive to an ambulatory surgery center while wearing a face mask. The patient can keep the mask on until the device is enclosed around them to prevent an instance of aerosolization or droplet transmission. The intubation/extubation can be performed inside the device and once the procedure is completed, a face mask can be applied to the patient. Accordingly, the device can reduce the risk of viral transmission before, during, and after patient care and allow for more rapid return of ambulatory surgery services.

The NPAM device can include a frame having one or more wall panels and struts. The internal chamber created by the frame can receive at least a portion of a patient's body, e.g., the head. A negative pressure can be generated within the internal chamber of the frame such that at least a portion of a patient's body is within a negative pressure environment. To contain the negative pressure, a drape can extend outwardly from an opening in the frame and can close the device around at least the portion of the patient's body. The drape can be flexible such that the extent to which it closes varies to accommodate different patients (e.g., adults, children, or animals of various sizes and shapes). The frame and neck drape can be sealed together to prevent fluid communication between the contained negative pressure environment and the external ambient environment. Both the frame and the drape can include transparent material to allow for interaction with the patient among providers.

Enclosing at least the head of a patient in the negative pressure environment can isolate a portion of the patient discharging biological contaminants. Instead of reaching the external ambient environment, biological contaminants are contained within the negative pressure environment. Additionally, enclosing a portion of the patient rather than their full body localizes the contained negative pressure environment to target certain discharge areas and prevent aerosolization. In addition, the smaller volume of the internal chamber enclosing a portion of the patient rather than their full body allows for efficient negative pressure generation, which can both quickly form and be sufficiently maintained.

In various embodiments, the NPAM device can be inflatable or rigid. The device can additionally be embodied by a non-rigid covering to adapt to different applications. Embodiments can be rapidly assembled, lightweight, and compactly packaged. The device can also have a long shelf life, and can be disposable (e.g., single-use), which can support mitigation of viral spread. Such features contribute to the portability and affordability such that the device can be impactful in containing viral spread.

In some embodiments, a negative pressure port disposed on the frame can create the negative pressure environment. A fitting removably attached to the negative pressure port can connect to a return air source (e.g., an air intake or suction device) to facilitate fluid communication with the contained environment for removal of air from the contained environment. Air in the contained environment can be directed to a return vent that is part of the HVAC system, a commercially available air vacuum, one or more fans, etc. Accordingly, lower pressure can be generated internal to the NPAM device in comparison to the ambient pressure of the environment outside of the contained environment, and the contained environment can be a negative pressure environment. The negative pressure port can additionally include a filter (e.g. a HEPA filter or other air filter) to collect particulates from the contained negative pressure environment. The device can also include one or more access ports to allow a provider to safely access and/or insert instruments into the contained negative pressure environment (e.g., in surgical applications). For example, performing various necessary elements of patient care can require providers to work closely to and/or engage the patient. Once a procedure and proper air recirculation and filtration are completed, a face mask can be applied to the patient and the device can be removed and disposed. In an embodiment, a wearable device (e.g., garment such as a "hoodie" type device) can be applied to the patient to further reduce the risk of viral transmission.

The device can be used in situations requiring rapid isolation of aerosolized or large particle pathogens or acute need of negative pressure environment with pathogen removal. Applicable industries include worldwide healthcare systems and military and disaster response management teams. Additional benefits also include a decrease in terminal cleaning time and a reduction in labor and supplies while simultaneously affording greater throughput through the hospital ward, emergency department or surgical ward. Because the device can remain in place for the duration of patient's care (e.g., hours, days, etc.), financial and environmental savings can be realized by reducing or eliminating the need for single-use PPE each time a provider interacts with the patient.

NPAM devices 50 described herein include, but are not limited to, an inflatable strut system 100 (FIGS. 1-6, 7, and 9), an inflatable strut system 200 (FIG. 6), a rigid strut system 1000 (FIG. 11), a tent system 2000 (FIGS. 16A-F), a rigid box system 3000 (FIG. 17), a wearable system 4000 (FIG. 18), and a mask system 5000 (FIGS. 19A-C). One or more NPAM device 50 can be to provide a contained negative pressure environment before, during, and/or after patient care.

Inflatable strut system 100, is shown in FIGS. 1A-D. Inflatable strut system 100 can move between a deflated state 10 (FIG. 2), an inflating state 20 (FIG. 3), and an inflated state 30 (FIGS. 1A-D; FIG. 4). Inflatable strut system 100 can have a front 101, a rear 102, a first side 103, and a second side 104. Inflatable strut system 100 can include a frame 110 and a drape 120. A negative pressure can be generated within frame 110, and drape 120 can extend outwardly from an opening in frame 110 to close its opening and contain the negative pressure. Frame 110 and drape 120 can be sealed together to prevent fluid communication between the contained negative pressure environment and the external ambient environment, as will be described below in further detail.

Frame 110 can include one or more wall panels 112 (e.g., floor, side, and ceiling wall panels 112), one or more frame seams 114, one or more air struts 116 (e.g., frame tubes), a main chamber 118, and an inflation port 130. Drape 120 can include a drape seam 122, a drawstring pocket 124, and a drawstring 126. In an embodiment, frame 110 and drape 120 can be transparent or translucent and can include plastic materials (e.g., medical grade plastic, thermosets, thermoplastics such as vinyl, ABS, or HDPE, etc.). Drape 120 can include a material restricting airborne particles greater than about 0.3 micron. In some embodiments, drape 120 can include a different material (e.g., a different plastic material) than frame 110. In some embodiments, the material of frame 110 can be less flexible than the material of drape 120. In some embodiments, drape 120 and frame 110 can both be a standard, inexpensive thermoplastic, such as ABS. In some embodiments, the thickness of frame 110 can be up to approximately 0.254 mm. In some embodiments, the thickness of drape 120 can be up to approximately 1.016 mm, such as approximately 0.076 mm. Accordingly, drape 120 can have a smaller thickness than frame 110.

Frame 110 can be a transparent barrier formed by wall panels 112, frame seams 114, and air struts 116. Each wall panel 112 can be a single layer of material. In an embodiment, frame 110 can be supported by approximately five wall panels 112. In an embodiment, frame 110 can include different numbers of wall panels 112 for different applications such that frame 110 can be adjustable and/or expandable. In another embodiment, each side of inflatable strut system 100—front 101, rear 102, first side 103, and second side 104—can include one or more wall panels 112. For example, front 101, first side 103, and second side 104 can include approximately one wall panel 112, and rear 102 can include approximately two wall panels 112. Each wall panel 112 can be separated from another wall panel 112 by an air strut 116. Frame seams 114 can join each wall panel 112 and air strut 116 to each other such that frame 110 can be unitary. In some embodiments, frame 110, including wall panels 112 and air struts 116, can be integrally formed or unitarily formed. In some embodiments frame seams 114 can utilize stitching and/or welding (e.g., mechanical or chemical fastening) to join wall panels 112 and air struts 116. Main chamber 118 can be formed within frame 110 and can be an internal volume of inflatable strut system 100. In some embodiments, frame seams 114 can be airtight such that they can prevent main chamber 118 from being in fluid communication with the external environment (i.e., the ambient environment external to inflatable strut system 100). Accordingly, frame seams 114 can create an airtight internal volume and can prevent fluid from flowing into or out of inflatable strut system 100.

Figure 1A:
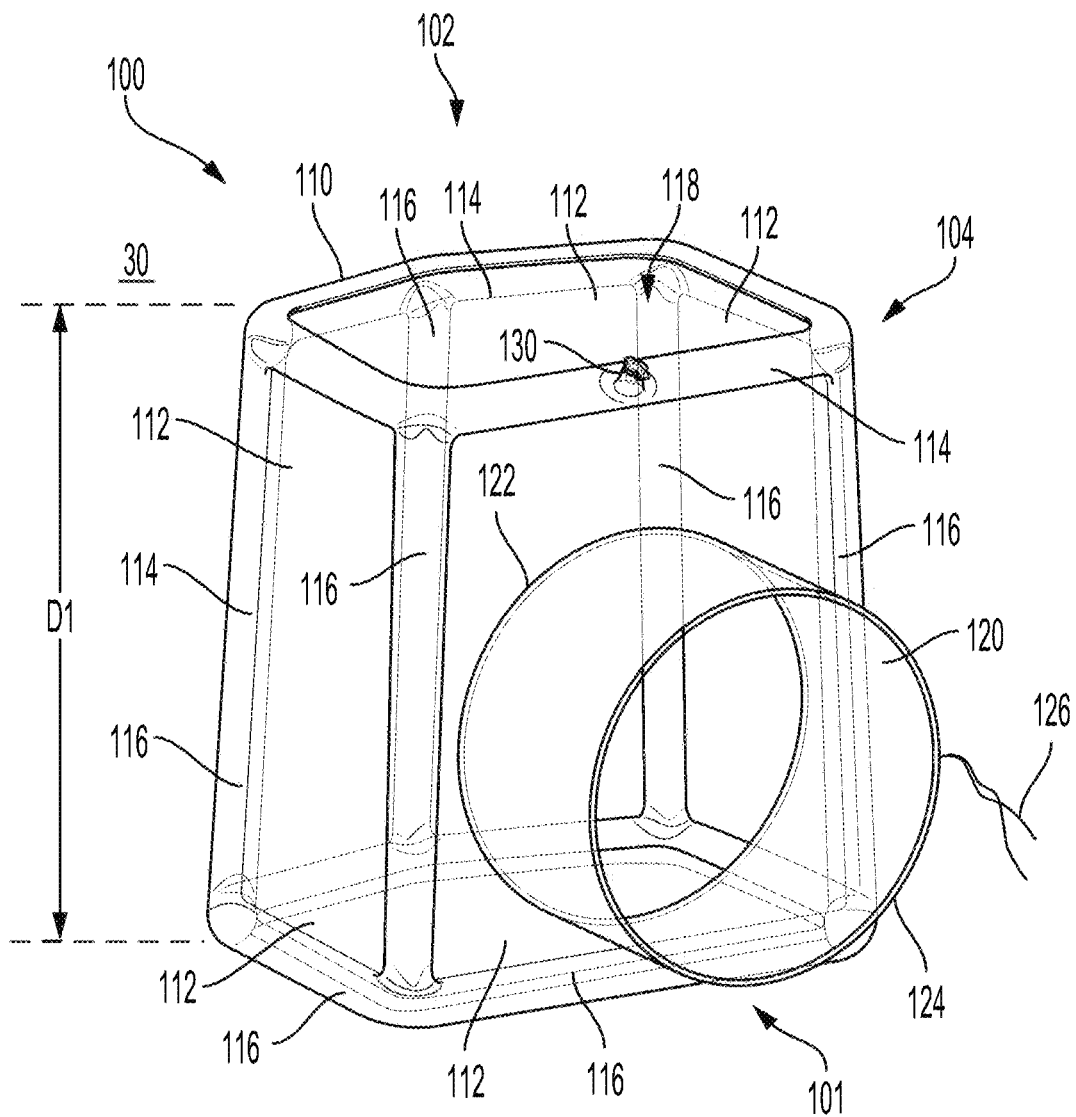
FIG. 1A is a perspective view of an inflatable NPAM device according to an embodiment.
Figure 1B:
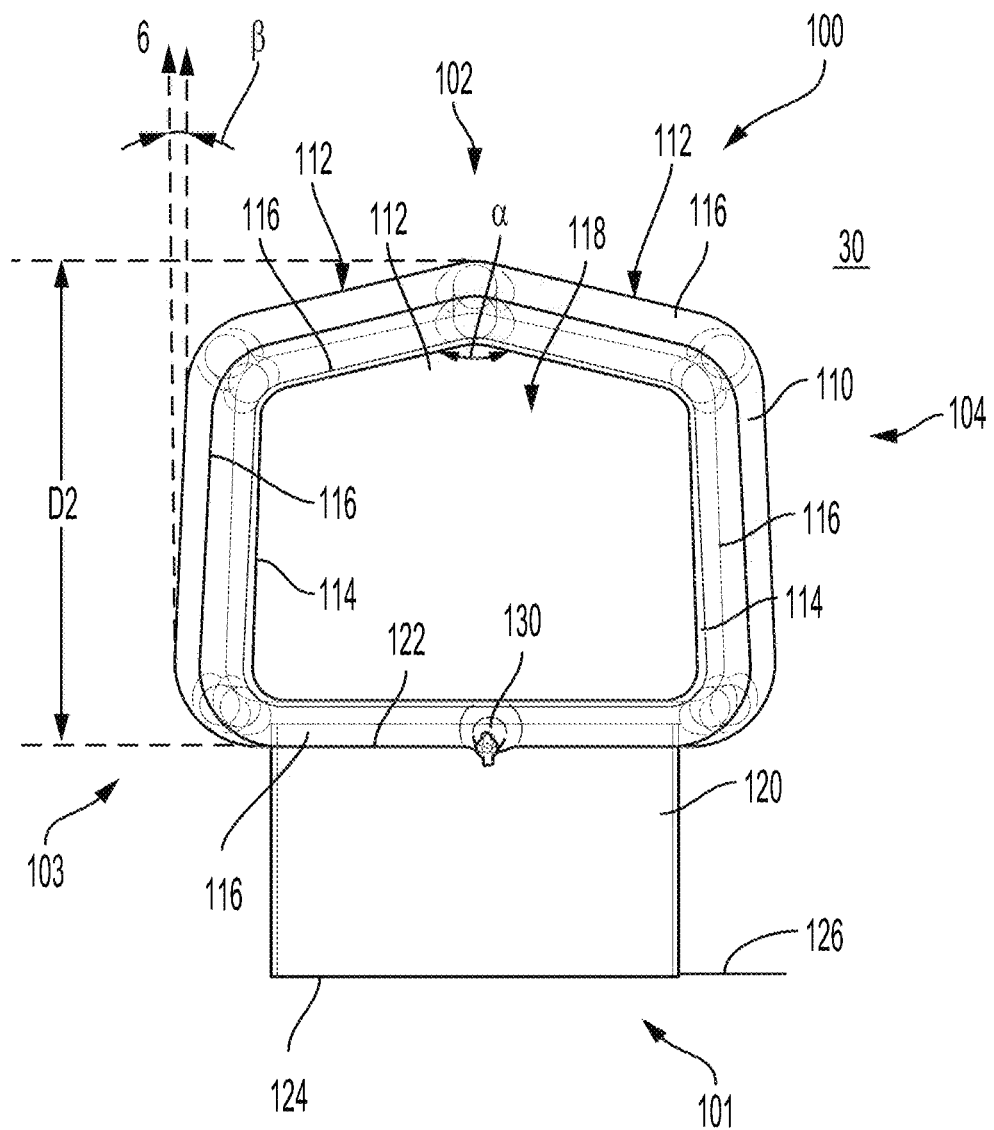
FIG. 1B is a top view of the inflatable NPAM device of FIG. 1A.
Figure 1C:
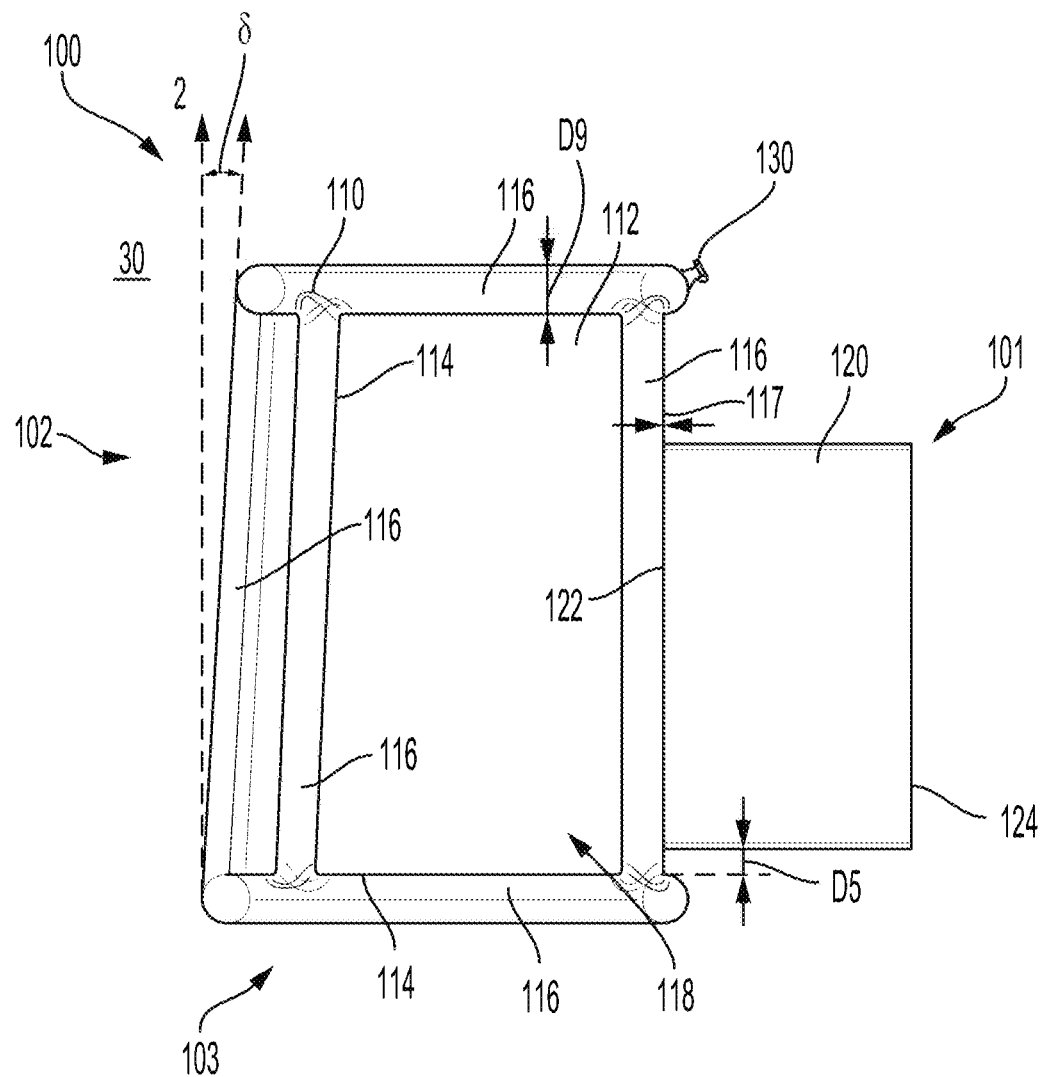
FIG. 1C is a side view of the inflatable NPAM device of FIG. 1A.

In addition, because frame 110 can be sealed from the external environment and air struts 116 can be in fluid communication with each other, inflatable strut system 100 can support a single inflation to move from deflated state 10 (FIG. 2) to inflated state 30 (FIGS. 1A-D; FIG. 4). As shown in FIG. 1B, inflation port 130 can be disposed on frame 110. In some embodiments, inflation port 130 can be disposed on a horizontally extending air strut 116 at the bottom right side of frame 110. A user can inflate inflatable strut system 100 via inflation port 130, which, in some embodiments, can be a one-way valve. In some embodiments, each air strut 116 can be hollow inflatable tubing in fluid communication with other air struts 116 such that a single inflation can inflate every air strut 116 at once. In this way, air struts 116 can be a common inflatable volume. As shown in FIG. 1B, inflation port 130 can be disposed on frame 110. A user can inflate inflatable strut system 100 via inflation port 130. Inflation port 130 can be fluidically connected to air struts 116 to inflate air struts 116 in fluid communication and move inflatable strut system 100 from deflated state 10 to inflated state 30. In some embodiments, inflation port 130 can be a one-way valve. Accordingly, air can easily flow into inflatable strut system 100 and backflow can be limited, requiring intentional actuation of inflation port 130 to achieve. As shown in FIG. 1C, in some embodiments, each air strut 116 can have a wall thickness 117 of approximately 0.10 mm to approximately 0.30 mm, such as approximately 0.20 mm. In some embodiments, air struts 116 can be rectangular, conical, pyramidal, and/or cylindrical in shape. In some embodiments, each air strut 116 can have a diameter, D10, of approximately 20 mm to approximately 40 mm, such as approximately 35 mm.

Figure 1D:
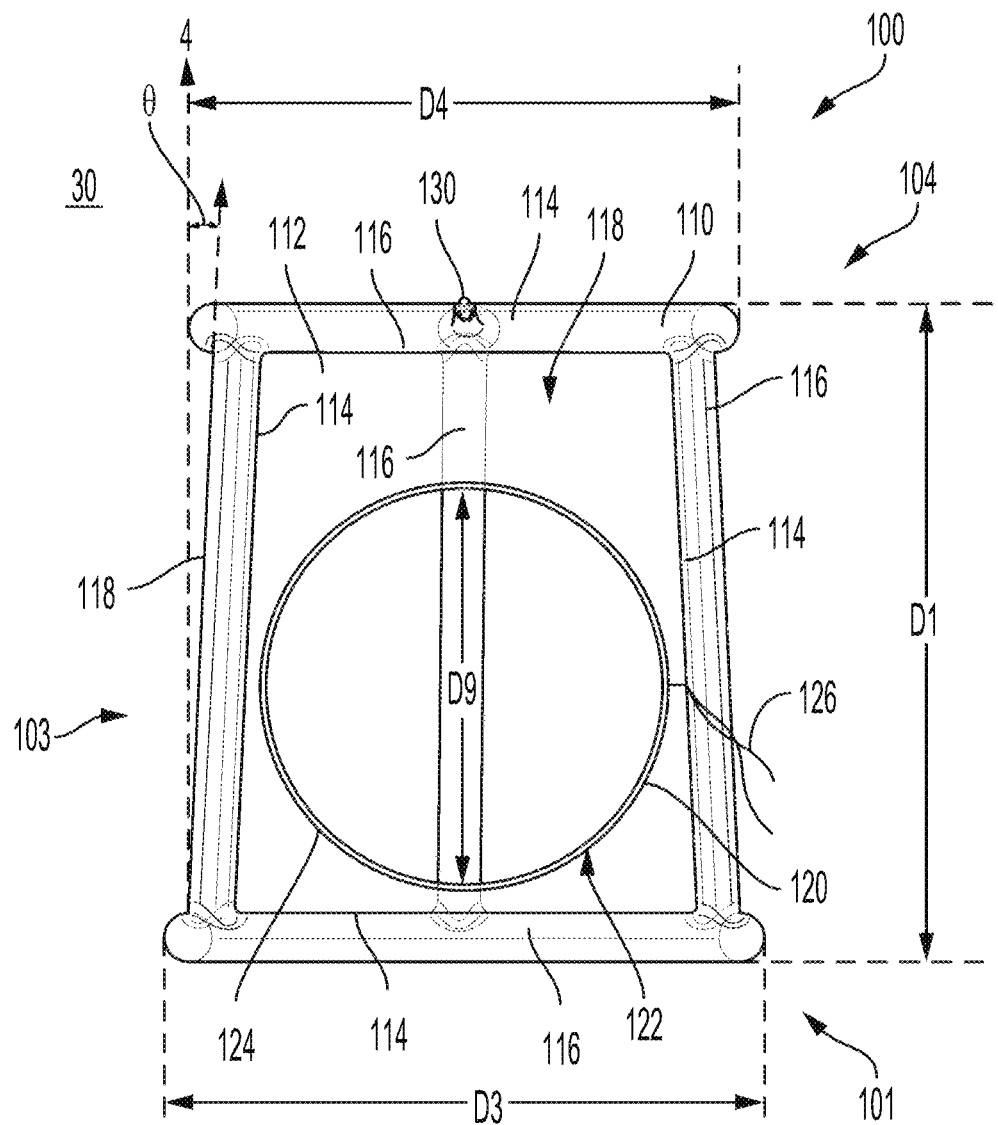
FIG. 1D is a front view of the inflatable NPAM device of FIG. 1A.

As shown in FIG. 1B, in some embodiments, rear 102 of inflatable strut system 100 can include approximately two wall panels 112. In an embodiment, the air strut 116 separating each wall panel 110 at rear 102 can have a diameter of approximately 25 mm. In another embodiment, wall panels 112 at rear 102 can form an angle, α, with each other. Angle, α, can be an obtuse angle. In some embodiments, the angle, a, can range from approximately 100 degrees to approximately 200 degrees, such as approximately 130 degrees to approximately 170 degrees, such as approximately 154 degrees. In some embodiments, each wall panel 112 at first side 103 and second side 104 can form an angle, β, from an axis 6 that can be generally perpendicular to a wall panel 112 at front 101. In some embodiments, the angle, β, can range from approximately 1 degree to approximately 20 degrees, such as approximately 2 degrees to approximately 10 degrees, such as approximately 5 degrees. As shown in FIG. 1C, in some embodiments, each wall panel 112 at rear 102 can form an angle, γ, from an axis 2 that can be generally perpendicular to a flat plane on which inflatable strut system 100 can be positioned. The angle, γ, can be an acute angle. In some embodiments, the angle, γ, can range from approximately 1 degree to approximately 20 degrees, such as approximately 2 degrees to approximately 10 degrees, such as approximately 3 degrees. As shown in FIG. 1D, in some embodiments, each wall panel 112 at first side 103 and second side 104 can form an angle, θ, from an axis 4 that can be generally perpendicular to a flat plane on which inflatable strut system 100 can be positioned. In some embodiments, the angle, θ, can range from approximately 1 degree to approximately 20 degrees, such as approximately 2 degrees to approximately 10 degrees, such as approximately 5 degrees.

With reference to FIGS. 1A and 1C, in some embodiments, first side 103 and second side 104 of inflatable strut system 100 can have a length, D1, in a longitudinal direction generally parallel to axis 2 of approximately 500 mm to approximately 550 mm, such as approximately 520 mm. With reference to FIG. 1B, in some embodiments, first side 103 and second side 104 can have a length, D2, in a transverse direction generally parallel to axis 6 of approximately 350 mm to approximately 400 mm, such as approximately 375 mm. With reference to FIG. 1D, in some embodiments, front 101 at a bottom of inflatable strut system 100 can have a length, D3, in a lateral direction generally perpendicular to axis 4 of approximately 470 mm to approximately 500 mm, such as approximately 480 mm. In some embodiments, front 101 at a top of inflatable strut system 100 can have a length, D4, in a lateral direction generally perpendicular to axis 4 of approximately 430 mm to approximately 500 mm, such as approximately 440 mm. In some embodiments, NPAM device 50, including inflatable strut system 100 can have a volume of approximately 82,250,000 mm$^3$ to approximately 110,000,000 mm$^3$.

With reference to FIGS. 1A and 1C, drape 120 can extend outwardly from an opening in frame 110 toward front 101 of inflatable strut system 100. The opening in frame 110 can be substantially circular, rectangular, or any other shape. Drape seam 122 can join drape 120 and frame 110 to each other such that inflatable strut system 100 having frame 110 and drape 120 can be unitary. For example, in some embodiments, drape seam 122 can be a continuous weld to join drape 120 and frame 110. In some embodiments, frame 110 and drape 120 can be integrally formed or unitarily formed. In some embodiments drape seam 122 can utilize stitching and/or welding (e.g., mechanical or chemical fastening) to join frame 110 and drape 120. The interior of drape 120 can be a volume that is in fluid communication with main chamber 118 of frame 110. Unlike frame 110, drape 120 does not inflate. Instead, drape 120 can be flexible such that it conforms its tubular shape around a portion of a patient, such as the neck or shoulders. The extent to which drape 120 closes can vary according to the patient. For example, the size of drape 120 can vary to accommodate adults, children, and/or animals of different shapes and sizes. Drape 120 can close around one or more type of patient or can be customized to fit (e.g., close around) one type of patient (e.g., adults, children, small animals, or large animals). Additionally, drape 120 can close around more than one patient (e.g., two patients, or portions of two patients).

With reference to FIG. 1D, at drape seam 122, drape 120 can have an effective diameter, D9, of approximately 300 mm to approximately 350 mm, such as approximately 310 mm. In some embodiments, drape 120 can instead be rectangular, conical, or pyramidal. With reference to FIG. 1C, drape 120 can be positioned at a length, D5, in a longitudinal direction generally parallel to axis 4 from a bottom air strut 116 of frame 110. Length, D5, can be up to approximately 30 mm, such as 23 mm.

Drape 120 can be cinched or drawn closed. At its front-most portion (e.g., front edge), drape 120 can include drawstring pocket 124. In some embodiments, drape 120 can be a single layer of material, however, drawstring pocket 124 can be a hollow portion of drape 120 that can receive drawstring 126, which can be a string, cord, rope, etc. Drawstring 126 can be threaded through drawstring pocket 124 such that it can be seated within drawstring pocket 124 almost entirely around drape 120 at its front-most portion. A portion of drawstring 126 can extend outwardly from drawstring pocket 124 to allow a user to pull the drawstring 126, thereby cinching or drawing closed drape 120. In some embodiments, drape 120 can additionally or alternatively include an elastic portion and/or adhesive to close. Closing drape 120 can converge the edges of the front most portion of drape 120 such that the internal volume of drape 120 is minimally or no longer in fluid contact with the ambient external environment.

Closing drape 120 can enclose the internal volume of inflatable strut system 100, thereby creating the contained environment. Applying a negative pressure system (e.g., negative pressure channel 140 in FIG. 7) can generate negative pressure in the contained environment such that inflatable strut system 100 supports a contained negative pressure environment. Once drape 120 is drawn closed or partially drawn closed, generating a negative pressure in the contained environment effectively suctions drape 120 to the patient. Accordingly, drape 120 further closes to maintain the contained negative pressure environment. If a patient or a portion of the patient is present within drape 120, generating a negative pressure in the contained environment effectively suctions drape 120 such that it seals around the patient or to the portion of the patient.

Drape 120 can be manufactured in multiple sizes to contain various internal volumes. For example, the size of drape 120 can vary based on the internal volume needed to contain a type of patient (e.g., adult, child, and/or animal). In other embodiments, drape 120 can be manufactured to contain an internal volume that can receive more than one type of patient. Additionally, drape 120 can be sized and/or shaped to accommodate more than one patient (e.g., two patients, or portions of two patients). Similarly, frame 110 can be sized and/or shaped to accommodate a patient. Frame 110 and/or drape 120 can be sized and/or shaped to accommodate any type of patient, including any of the patients described herein (e.g., a portion of a single patient, a single patient's entire body, portions of multiple patients, multiple patients, adult or pediatric patients, veterinary patients, etc.).

Figure 2:
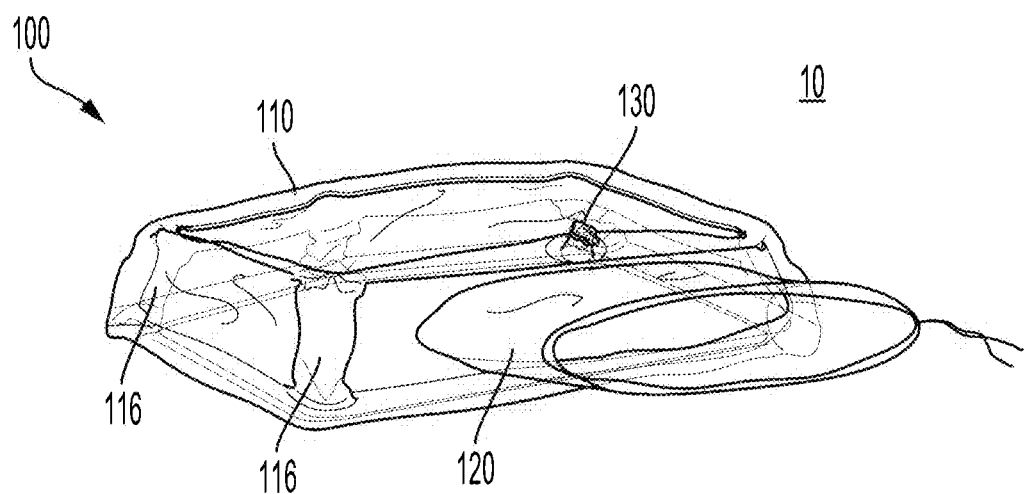
FIG. 2 is a perspective view of the inflatable NPAM device of FIG. 1A in a deflated state.
Figure 3:
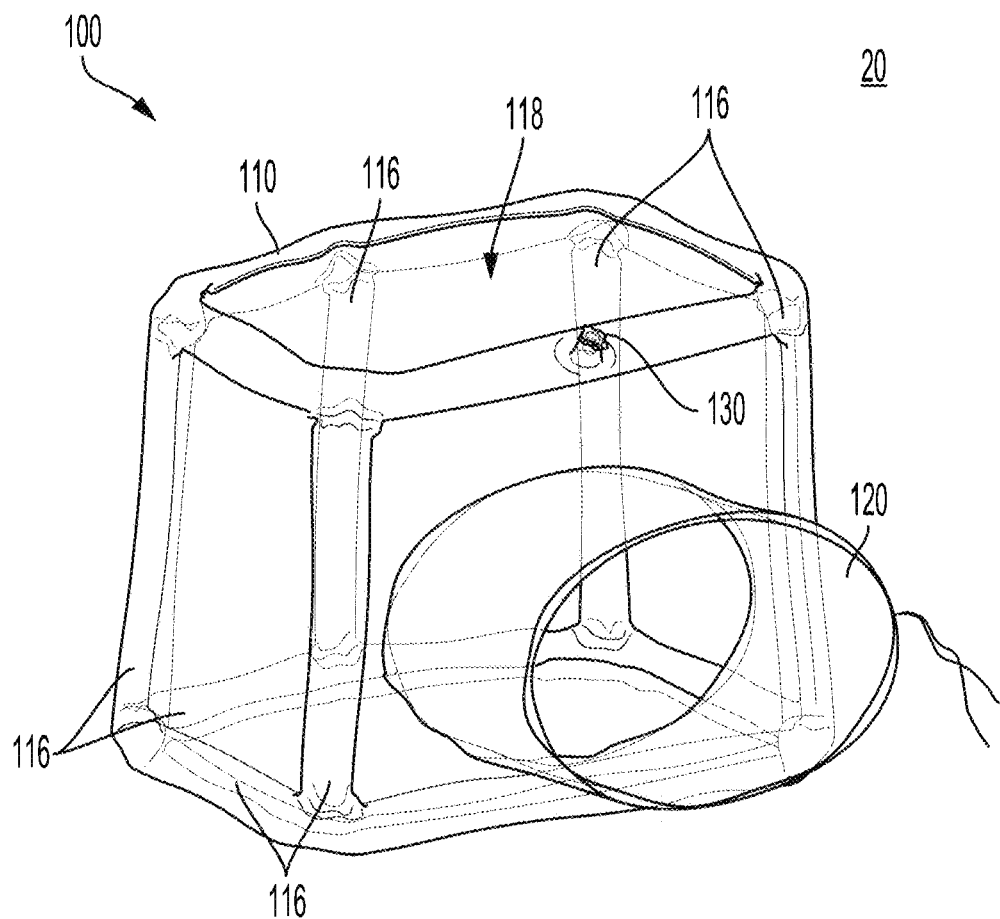
FIG. 3 is a perspective view of the inflatable NPAM device of FIG. 1A in an inflating state.
Figure 4:
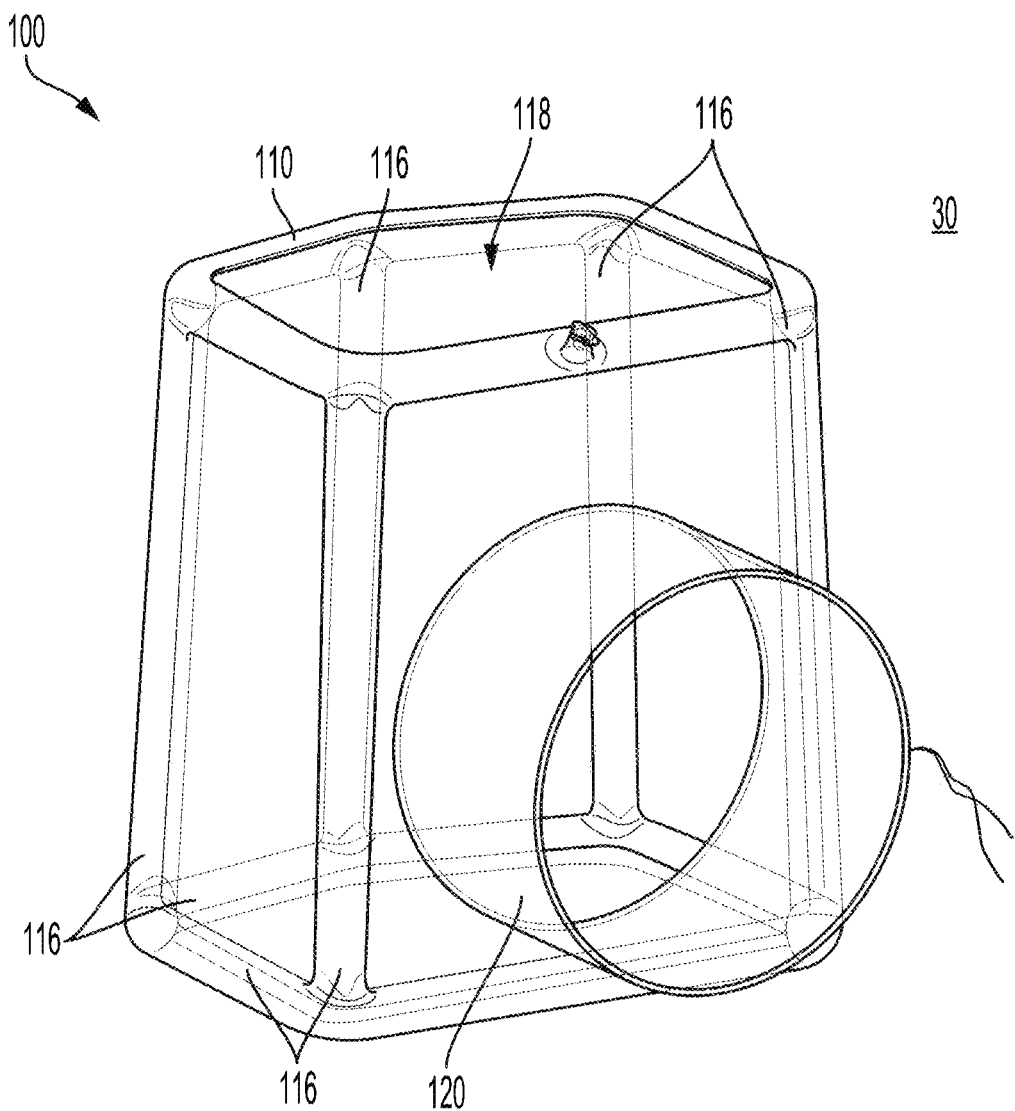
FIG. 4 is a perspective view of the inflatable NPAM device of FIG. 1A in an inflated state.

FIGS. 2-4 show inflatable strut system 100 in deflated state 10 (FIG. 2), inflating state (FIG. 3), and inflated state 30 (FIG. 4). As discussed above, inflation port 130 can facilitate inflation of inflatable strut system 100 by being fluidically connected to air struts 116 of inflatable strut system 100. As shown in FIG. 3, in deflated state 10, air struts 116 can have minimal internal volumes such that inflatable strut system 100 can be deflated. In deflated state 10, inflatable strut system 100 can be non-rigid and compactable, which can support portability, transportation, etc. As discussed above, drape 120 can be flexible such that it can be foldable to compactly package inflatable strut system 100. As shown in FIG. 3, an air supply can be provided to each individual air strut 116 via inflation port 130. Because air struts 116 are in fluid communication and, thus, are a common inflatable volume, a single air supply can inflate all air struts 116 at once. In some embodiments, air can be physically blown into inflation port 130 by an individual or the air supply can be provided by another device, such as an air pump (e.g., an electrical air pump, a bike pump, CO2 cartridge, oxygen tank, etc.) via inflation port 130.

As shown in FIG. 3, as air struts 116 are filled with air in inflating state 20, inflation system 100 can expand. In some embodiments, as air struts 116 are filled with air, visual feedback can indicate that air struts 116 can continue to receive air to become inflated. As shown in FIG. 4, in inflated state 30, air struts 116 can be sufficiently inflated. In some embodiments, visual and/or tactile feedback can be provided to indicate that air struts 116 are sufficiently inflated. For example, in inflated state 30, air struts 116 can appear through visual and/or tactile feedback to be semi-rigid or rigid such that they cannot be folded or collapsed and main chamber 118 is maintained. In some embodiments, inflatable strut system 100 can be rapidly inflated. For example, inflation to inflated state 30 can take up to approximately 1 minute, e.g., approximately 45 seconds. In this way, inflatable system can be useful to quickly provide patient care and mitigate communicable disease transmission risks. Rapid patient containment and negative pressure environment generation can be important during periods of high patient care volume, such as pandemics, to mitigate transmission and maintain provider safety. Air struts 116 can be filled with air when a patient or a portion of a patient is already contained within frame 110. Otherwise, air struts 116 can be filled with air until sufficiently inflated, for example, and thereafter, a patient or a portion of a patient can be received. In some embodiments, a pressure sensor can prevent over inflating inflatable strut system 100 by providing a pressure measurement of air struts 116 and therefore, inflatable strut system 100. The pressure measure can indicate that inflatable strut system 100 is sufficiently inflated.

Inflation port 130 can be closed to prevent air from being released and to maintain inflatable strut system 100 in inflated state 30. Inflation port 130 can be opened to release air from air struts 116 and deflate inflatable strut system 100 (e.g., move from inflated state 30 to deflated state 10). Air can be released from air struts 116 via inflation port 130 in the same way that air is supplied to air struts 116, e.g., via a conventional air pump. Air can also be pushed out of air struts 116 via inflation port 130. In this way, inflatable strut system 100 can be easily packaged and/or stored for reuse. Inflatable strut system 100 can also be disposed easily after deflation.

Figure 5:
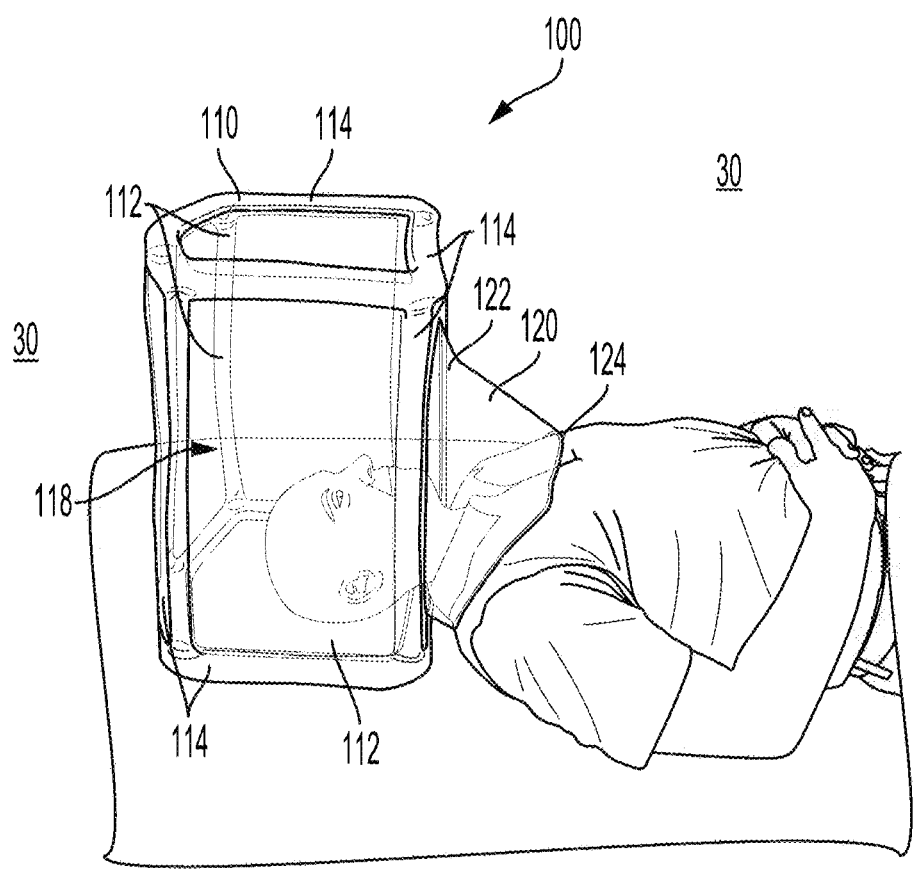
FIG. 5 is a perspective view of a patient and the inflatable NPAM device of FIG. 1A.

As shown in FIG. 5, in inflated state 30, inflatable strut system 100 can receive a patient's entire body or a portion of a patient's body (e.g., their head, arm, or leg, etc.). In some embodiments, the portion of the patient received in inflatable strut system 100 can be of interest for monitoring or treatment in a healthcare environment (e.g., for triage, critical care, endotracheal intubation and extubation, bronchoscopy, hemodynamic monitoring invasive catheterization, esophagogastroduodenoscopy (EGD), transesophageal echocardiography (TEE), procedures involving the ear, nose, and throat, and Advanced Cardiovascular Life Support (ACLS) procedures). For example, if the patient is to undergo dental treatment, at least the patient's head can be contained within inflatable strut system 100. In another example, if the patient is to undergo surgery on their foot, at least the patient's foot (e.g., up to their ankle or knee) can be contained within inflatable strut system 100. Accordingly, at least a portion of the patient can be isolated in the negative pressure environment contained within inflatable strut system 100, which can prevent aerosolized biological contaminants from reaching the external ambient environment.

Additionally, the portion of the patient's body received in inflatable strut system 100 can be defined in terms of mitigating the risk to providers in the vicinity of the patient from aerosolization and droplet transmission. For example, if the patient is experiencing respiratory issues associated with an active pandemic, for example, or was exposed to a communicable disease, at least the patient's head can be contained within inflatable strut system 100 to retain and exhaust respiratory droplets. In some examples, even if the patient is not experiencing respiratory issues or was exposed to a communicable disease, NPAM device 50, including inflatable strut system 100, can allow low risk patients to undergo elective and non-elective surgeries or procedures. In this way, both the patient and providers can be protected from transmission risks and elective and non-elective surgeries or procedures can proceed during a pandemic, for example. In some embodiments, inflatable strut system 100 can receive a patient's entire body. In some embodiments, inflatable strut system 100 can receive at least the patient's head up to approximately their entire torso. Accordingly, the portion of the patient's body within main chamber 118 can include the patient's neck. In some embodiments, a neck rest (e.g., a foam neck rest) can be disposed in main chamber 118 to provide support to the patient's neck and head within NPAM device 50.

NPAM device 50, including inflatable strut system 100, can also be useful in pediatric applications. For example, main chamber 118 can include an internal volume sufficient to support an iPad (or other user device, e.g., tablet, phone, computer, etc.) and an attachment for securing the iPad to inflatable strut system 100 (e.g., onto the inside of frame 110). Accordingly, pediatric patients who are at least partially contained in inflatable strut system 100 (e.g., up to their torso) can have their arms and hands within the contained negative pressure environment to use the iPad while awaiting a pediatric sedation event, for example. In this way, transmission of communicable diseases can be mitigated because the patient is contained within a negative pressure environment, and the pediatric patient can be positively engaged and distracted while awaiting sedation. In some embodiments, the attachment can be used to support tools or instruments for use in patient care.

In another example, NPAM device 50, including inflatable strut system 100, can facilitate veterinary applications. Negative pressure environments can support veterinary patient care, such as for wound management. The negative pressure can protect the wound and support drainage and healing. Thus, a veterinary patient can be contained within the negative pressure environment of inflatable strut system 100 to accelerate healing. Treatment can accompany the negative pressure environment containment to advance care. The adjustability, expandability, and portability of NPAM device 50, including inflatable strut system 100, is useful in veterinary applications where the veterinary patient can range in size and can be located in various settings (e.g., natural habitat, veterinary clinic, housing, etc.).

In other examples, NPAM device, including inflatable strut system 100, can be used in environments where portable treatment options are desirable, such as, for example, sports events or other large gatherings, travel (e.g., air travel), schools, offices, shopping centers, parks, or even space travel, or any other public or private application to achieve NPAM device 50 benefits described herein. The compact packaging, lightweight, portability, and single-use aspects of NPAM device 50 allow for its usability in a variety of applications. For example, in air travel, quick access to NPAM device 50 is convenient because alternative healthcare options can be limited. And with regard to space travel, mitigating potential hazards related to pathogens aerosolizing and infecting other crew members without additional resources or access to hospitals in a confined area, NPAM device 50 is an option to reduce exposure risk.

In some embodiments, at least a portion of the patient's body can be received in inflatable strut system 100 such that at least the portion of the patient's body is within main chamber 118. Accordingly, main chamber 118 can form a volume around the portion of the patient's body. In some embodiments, at least a portion of the patient's body (e.g., their neck, hand, foot, etc.) can be within the internal volume of drape 120. As discussed above, drape 120 can be cinched or drawn closed. Accordingly, inflatable strut system 100 can receive a portion of the patient's body or their entire body and drape 120 can be closed around the patient such that at least a portion of the patient is enclosed within inflatable strut system 100. Thus, inflatable strut system 100 can create a contained negative pressure environment in which a patient is received. In some embodiments, enclosing at least a portion of a patient within the negative pressure environment of inflatable strut system 100 can isolate the patient with respect to the volume surrounding them. In this way, the portion of the patient within the negative pressure environment of inflatable strut system 100 can be isolated from the ambient external environment.

In some embodiments, inflatable strut system 100 can receive at least the patient's head up to approximately their entire torso, e.g., at least the patient's head and neck. In some embodiments, the patient's entire body may be received in inflatable strut system 100.

Figure 6:
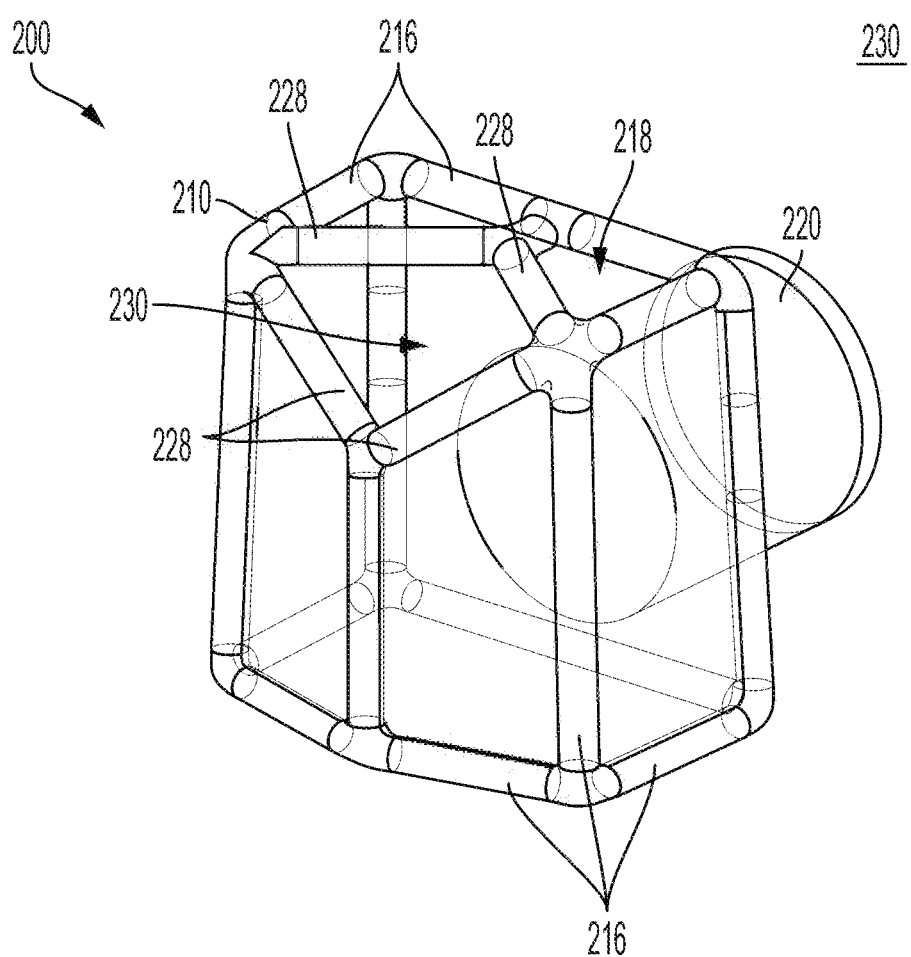
FIG. 6 is a perspective view of an inflatable NPAM device according to an embodiment.

As shown in FIG. 6, NPAM device 50 can be inflatable strut system 200 that can correspond to inflatable strut system 100 (FIGS. 1A-6). Inflatable strut system 200 can include one or more air struts 216 that can correspond to air struts 116. One or more air struts 216 can form an upper geometry that provides a line of sight into main chamber 218. For example, air struts 228 can outline a generally rectangular shape on frame 210 to provide a window 230. Window 230 can provide a large and/or unobstructed view of the portion of the patient positioned within main chamber 218 of inflatable strut system 200 during patient care. Accordingly, window 230 can improve patient care by widening the field of vision of the practitioner. In some embodiments, air struts 228 can outline a generally circular or any other shape on frame 210 to provide window 230. For example, air struts 228 can form a Y-shape. In some embodiments, frame 210 can support more than one window 230 to provide multiple points of improved vision to the practitioner.

Figure 7:
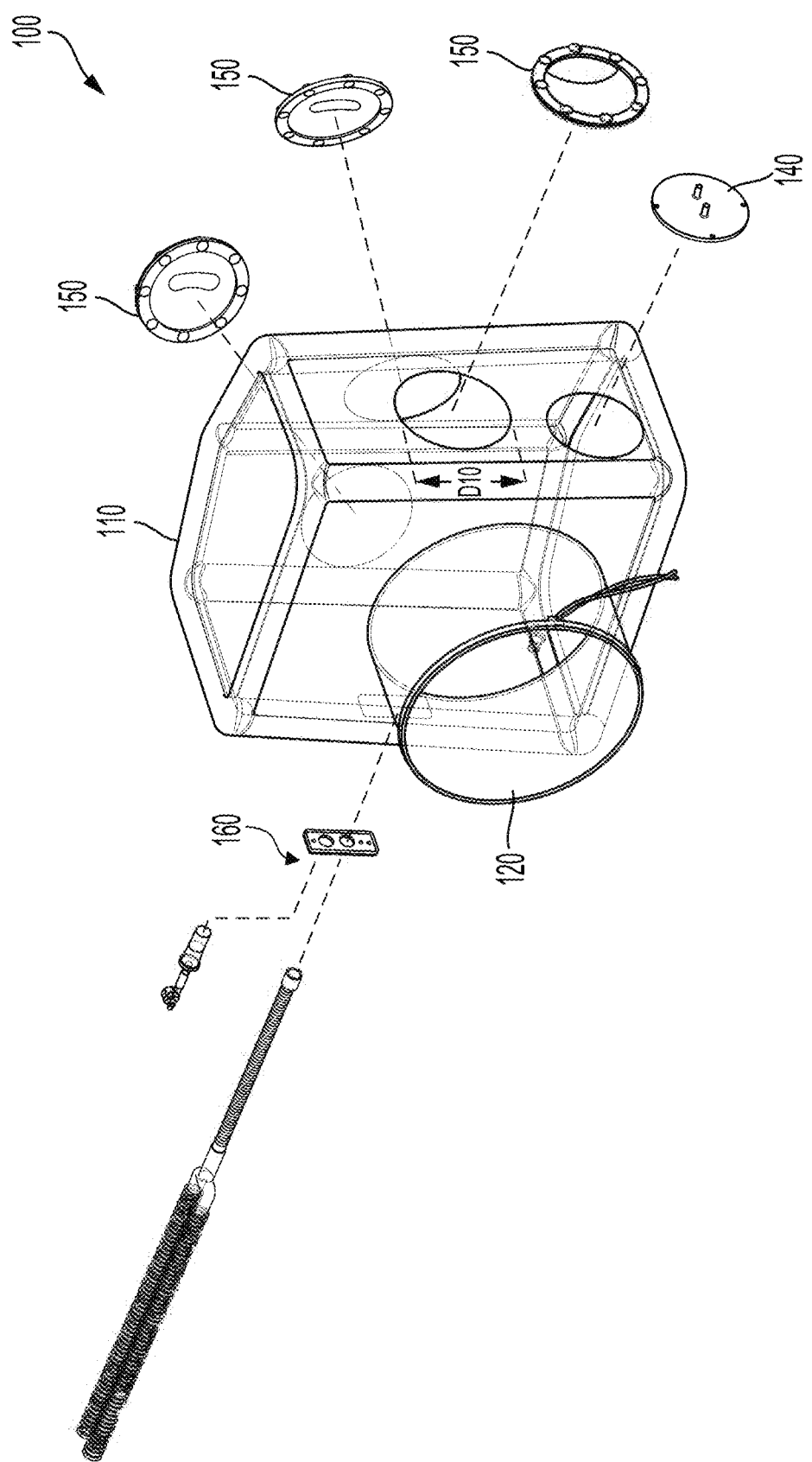
FIG. 7 is an assembly view of an inflatable NPAM device according to an embodiment.

As shown in FIG. 7, in some embodiments, inflatable strut system 100 can include frame 110, drape 120, and one or more openings. The one or more openings can be utilized by a provider for at least access, instrument passage and use, connection to air return or suction to create a negative pressure environment, oxygenation, and/or a waste receptacle. In some embodiments, each opening can have an effective diameter, D10, of approximately 3 inches to approximately 15 inches (0.0762 mm to approximately 38.1 mm). In some embodiments, inflatable strut system 100 can include one or more negative pressure channels 140, one or more access ports 150, and/or one or more manifolds 160, which will be described in detail below.

In some embodiments, frame 110 and drape 120 can be a base assembly that can be customized according to a specific application. For example, as discussed above, NPAM devices 50 including inflatable strut system 100 can be used in a variety of applications, e.g., triage, emergent critical care procedures, elective, and some non-elective surgeries, for pediatric or veterinary applications, etc. According to a specific application, one or more negative pressure channels 140, one or more access ports 150, and/or one or more manifolds 160 can be added. In some embodiment, the size of the openings receiving these components can be varied based on the application of inflatable strut system 100 and the configuration added to the base assembly. A wall panel 112 of frame 110 can receive one or more negative pressure channels 140, one or more access ports 150, and/or one or more manifolds 160. Accordingly, a negative pressure channel 140, an access port 150, and/or a respiratory port can be disposed on wall panel 112. In some embodiments, the customization can be prefabricated onto the base assembly (e.g., the base assembly of frame 110 and drape 120 can be prefabricated to include one or more negative pressure channels 140, one or more access ports 150, and/or one or more manifolds 160).

Figure 8:
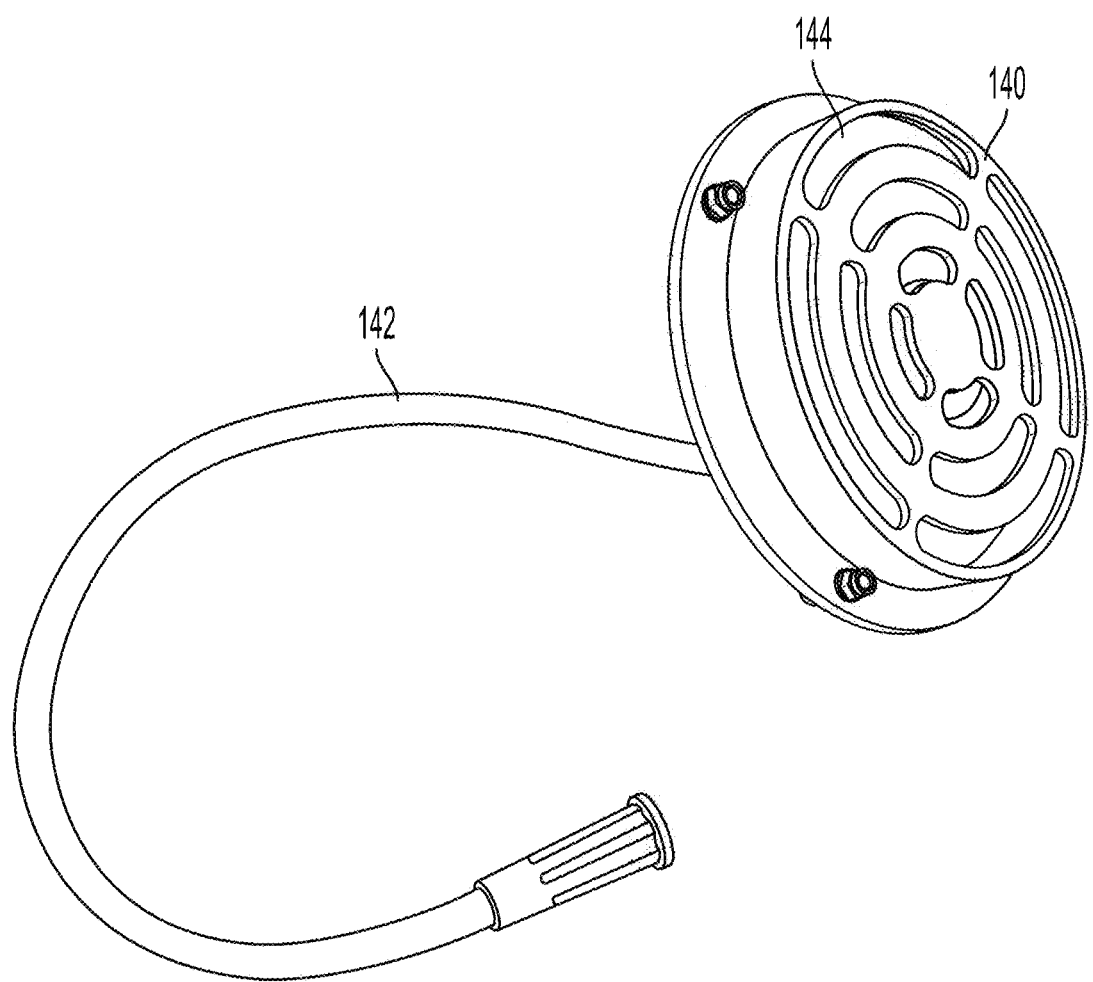
FIG. 8 is a perspective view of an exhaust system according to an embodiment.

As shown in FIG. 8, in some embodiments, negative pressure channel 140 can include a fitting 142 and/or a filter 144. Negative pressure channel 140 can open into a wall panel 112 of frame 110 (FIG. 7) and can include fitting 142 on its outer surface. Negative pressure channel 140 can suction air internal to frame 110 (e.g., within main chamber 118) to generate a lower pressure inside the contained environment as compared to an ambient pressure of the external environment. Accordingly, the contained environment can be a negative pressure environment. In some embodiments, the contained negative pressure environment can have a pressure differential greater than approximately −2.5 Pa.

In some embodiments, fitting 142 can be operatively coupled to an air return (not shown). In some embodiments, fitting 142 can be removably coupled to an external suction device (not shown) to allow fluid communication with the contained negative pressure environment within inflatable strut system 100. The external suction device can facilitate generating negative pressure within the contained environment. In an embodiment, fitting 142 can be compatible with hospital or other commercially available, compatible, suction devices (e.g., a vacuum pump). Fluid communication between an external suction device and the contained negative pressure environment allows for removal of air from the contained negative pressure environment, which can retain biological contaminants from a patient within the contained negative pressure environment for subsequent discharge. In this way, biological contaminants are not dispersed to the external ambient environment. In some embodiments, negative pressure channel 140 can extend into the contained negative pressure environment to a position that is proximate to a face of the patient. Accordingly, biological contaminants from a patient can rapidly interact with a negative air pressure for retention once discharged by the patient via their mouth, for example.

In an embodiment, negative pressure channel 140 can have a fitting 142 that can be compatible with biohazard PAPR hose connections in the negative pressure configuration. The PAPR can be connected via tubing which can allow a provider to place an external suction device in a convenient location in the external environment. In some embodiments, filter 144 can be attached on the inner surface of negative pressure channel 140. In some embodiments, filter 144 can be a commercially available viral filter, such as N95 or HEPA filters with effectiveness to less than 0.3 microns. In some embodiments, filter 144 can instead be attached to the fan unit of a PAPR, an external suction device, and/or an air return. Proper air removal via negative pressure channel 140 mitigates the risk of airborne transmission to those proximate to the patient. In addition, proper connection of filter 144 allows for adequate aerosolization prevention. In some embodiments, the one or more openings of NPAM device 50, including inflatable strut system 100 can include a filter 144 to prevent aerosolized particle from exiting NPAM device 50 through any one of the openings. Negative pressure channel 140, fitting 142, and filter 144 can be integral. In this way, it is possible for those components to be commercially sourced together.

Figure 9:
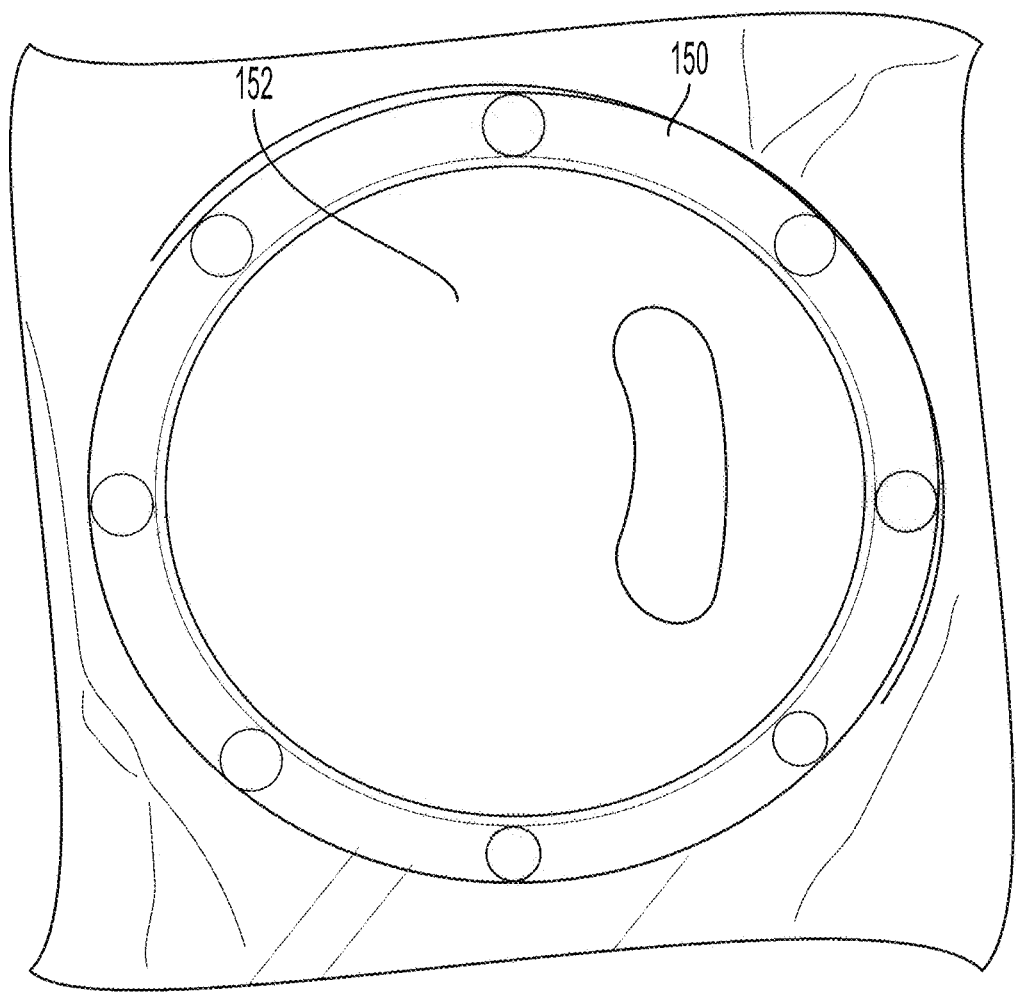
FIG. 9 is a perspective view of an access port according to an embodiment.

As shown in FIG. 9, in some embodiments, access port 150 can include a flow limited passageway 152. Flow limited passageway 152 can limit or prevent ingress and egress of air such that the negative pressure environment within inflatable strut system 100 is maintained and biological contaminants from a patient are not dispersed to the external ambient environment. Access port 150 can allow a provider to access a portion of a patient within the contained negative pressure environment. For example, a provider can push their hands or arms through access port 150 to reach the head or chest area of the patient. In some embodiments, access port 150 can be a disc-shaped grommet that can define the entry opening for accessing the negative pressure environment. The grommet can accommodate flow limited passageway 152 such as by having a lip that can receive and clamp flow limited passageway 152. Accordingly, flow limited passageway 152 can facilitate access through a wall panel 112 of frame 110 (FIG. 7) to the contained negative pressure environment within inflatable strut system 100. Flow limited passageway 152 can be biased to or have a normal or initial position that is sealed or fills the grommet. In some embodiments, the grommet can include nylon, and flow limited passageway 152 can include silicone rubber.

In some embodiments, flow limited passageway 152 can be a one-way, self-sealable valve having an entry denial system after negative pressure, which can prevent air from traveling from the contained negative pressure environment to the ambient external environment even if a provider passes their hands or arms through access port 150. For example, the one-way valve can be an elastic duckbill valve that can allow movement in one direction (e.g., into the contained negative pressure environment) and prevent movement in the opposing direction (e.g. into the ambient external environment). In some embodiments, flow limited passageway 152 can include a breakable seal such that flow limited passageway 152 is closed until pierced by a provider for access to the contained negative pressure environment. In some embodiments, the breakable seal can extend across access port 150 and can have pre-formed slits to support piercing of flow limited passageway 152. In some embodiments, flow limited passageway 152 can include a flap that can be opened to allow a provider access to the contained negative pressure environment. In some embodiments, flow limited passageway 152 can include pliable plastic components (e.g., gloves or other protective equipment) that can conform to a provider's hands or arms upon entry.

In some embodiments, flow limited passageway 152 can be a pliable disc having one or more slits intersecting in a center portion forming partial segments of the pliable disc. The partial segments of the pliable disc can flex to allow passage of at least a hand of a provider into the contained negative pressure environment and can close when the at least the hand of the provider is removed from the contained negative pressure environment. In some embodiments, flow limited passageway 152 can be a loose fitting material secured to a ring and having a center aperture. The ring can allow passage of at least a hand of a provider into the contained negative pressure environment and the loose fitting material can extend into the contained negative pressure environment such that at least a portion of an arm of the provider is protected by the loose fitting material. In some embodiments, an elastic cuff (not shown) at the center aperture can partially close a gap between the at least a portion of the arm of the provider and the center aperture.

In some embodiments, access port 150 can be sized and/or shaped to facilitate transportation of one or more instruments from the external environment to the contained negative pressure environment. For example, an access port 150 for utility can be added to the base assembly of frame 110 and drape 120 to allow for the sterile passage of medical equipment. In dentistry, for example, utility access ports 150 can allow for passage of teeth cleaning equipment (e.g., a water sprayer, scraper, floss, etc.). For wound care, utility access ports 150 can allow for passage of antiseptic wipes, bandages, etc. In pediatrics, utility access ports 150 can allow for passage of an iPad or other device for use by the pediatric patient. For general patient care accessible to patients at low risk for transmitting or contracting communicable diseases, utility access ports can allow for passage of stethoscopes, thermometers, otoscopes, etc.

In some embodiments, inflatable strut system 100 can include approximately two access ports 150 for provider access and approximately two access ports 150 for instrument access. In some embodiments, the access ports 150 for instrument access can be sized to allow an assistant to enter the contained negative pressure environment to add or remove instruments for use by a provider in the contained negative pressure environment.

Figure 10:
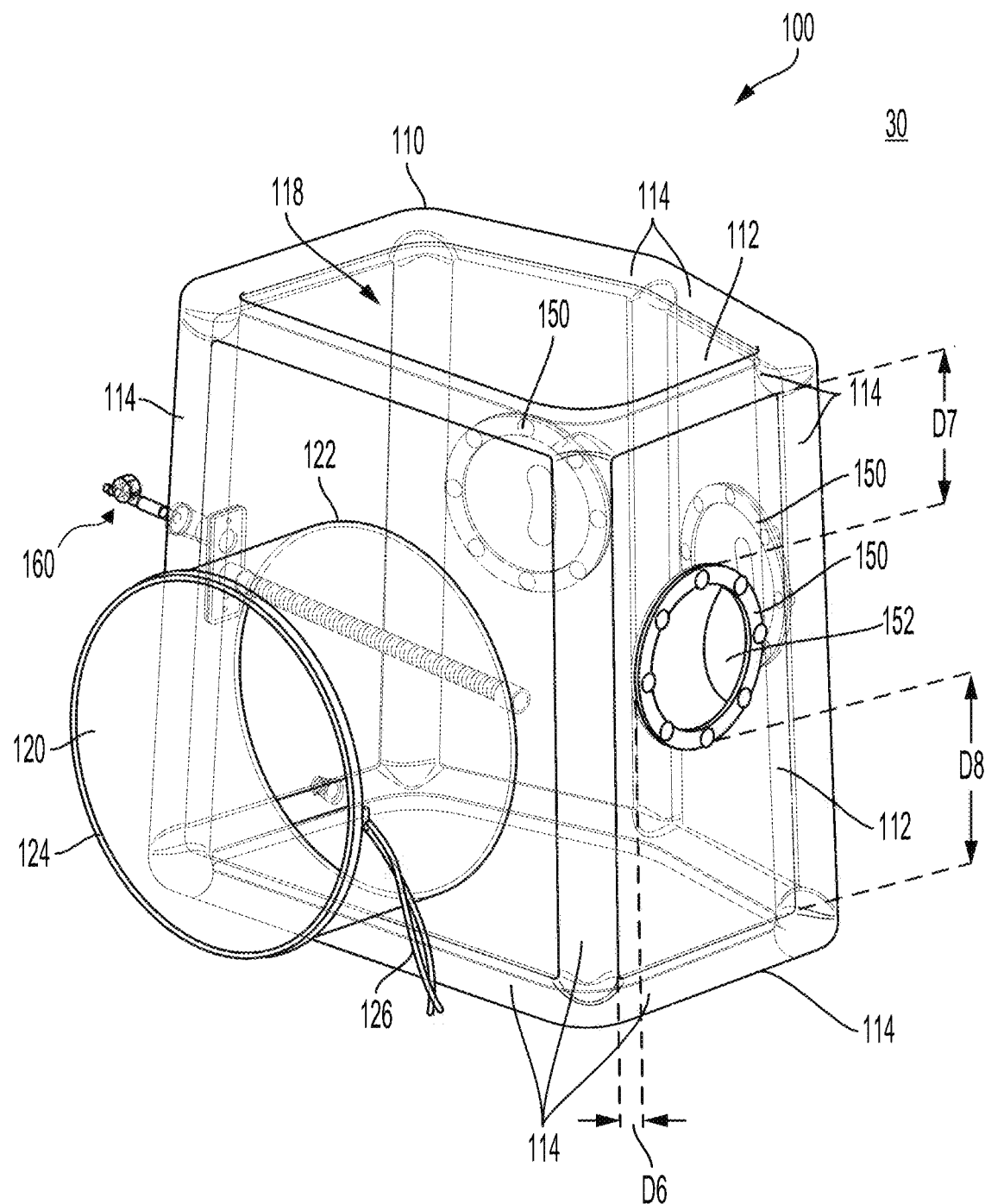
FIG. 10 is a perspective view of the inflatable NPAM device of FIG. 7.

As shown in FIG. 10, access port 150 can be positioned in a center of a wall panel 112 of frame 110. In some embodiments, access port 150 can be at a distance, D6, from a side edge of a wall panel 112. In some embodiments, access port 150 can be at a distance, D7, from a top edge of a wall panel 112. In some embodiments, access port 150 can be at a distance, D8, from a bottom edge of a wall panel 112. In some embodiments, access port 150 can be customized for inflatable strut system 100. For example, the number of access ports 150 can be varied based on the specific application of inflatable strut system 100, such as approximately two access ports 150 to approximately six access ports 150, such as approximately three access ports 150. Additionally, the position of an access port 150 can be defined based on the specific application of inflatable strut system 100. In an example, for an application requiring patient contact, one or more access ports 150 can be positioned lower on a wall panel 112 to allow access to the contained negative pressure environment near the patient's head or chest. In another example, for an application requiring both patient contact and instruments (e.g., dentistry), an access port 150 for utility can be positioned higher on a wall panel 112 to allow an access port 150 for entry to be positioned lower on the wall panel 112. In a pediatric application, an access port 150 can be positioned higher on a wall panel 112 to facilitate access to a higher positioned iPad support disposed on the interior of frame 110, for example. Accordingly, a provider or assistant can easily secure or remove the iPad on the support via access port 150.

In some embodiments, a waste receptacle (not shown) can be disposed on a wall panel 112 of frame 110. In some embodiments, the waste receptacle can be a disposable bag (e.g., a plastic, biodegradable, or compostable bag, etc.). In some embodiments, the waste receptacle can be sealingly secured to a wall panel 112 and can be accessible from within the contained negative pressure environment. In some embodiments, the waste receptacle can be configured to protrude beyond the outer surface of inflatable strut system 100. In some embodiments, the waste receptacle can contain a volume of medical waste. In some embodiments, the waste receptacle can be pre-attached and can be invertible (e.g., items can be dropped into the bag by a hand on the inside while the bag is located on the outside).

Figure 11:
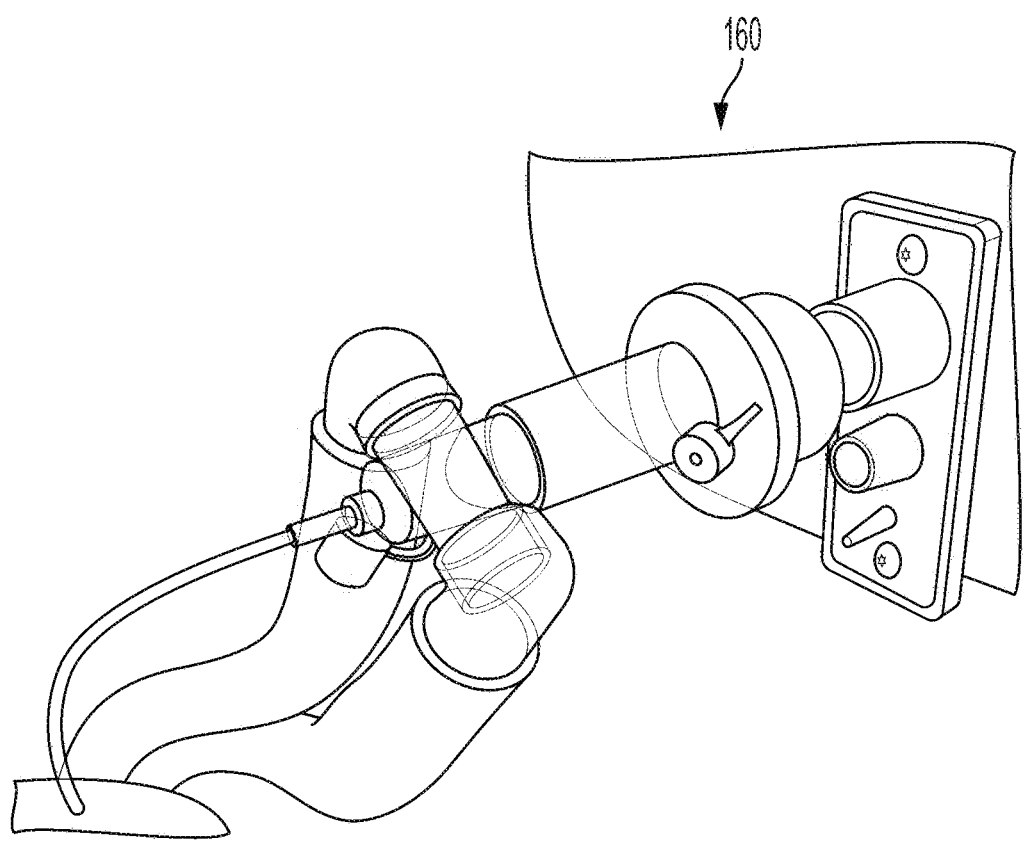
FIG. 11 is a perspective view of a respiratory and pressure manifold according to an embodiment.
Figure 12:
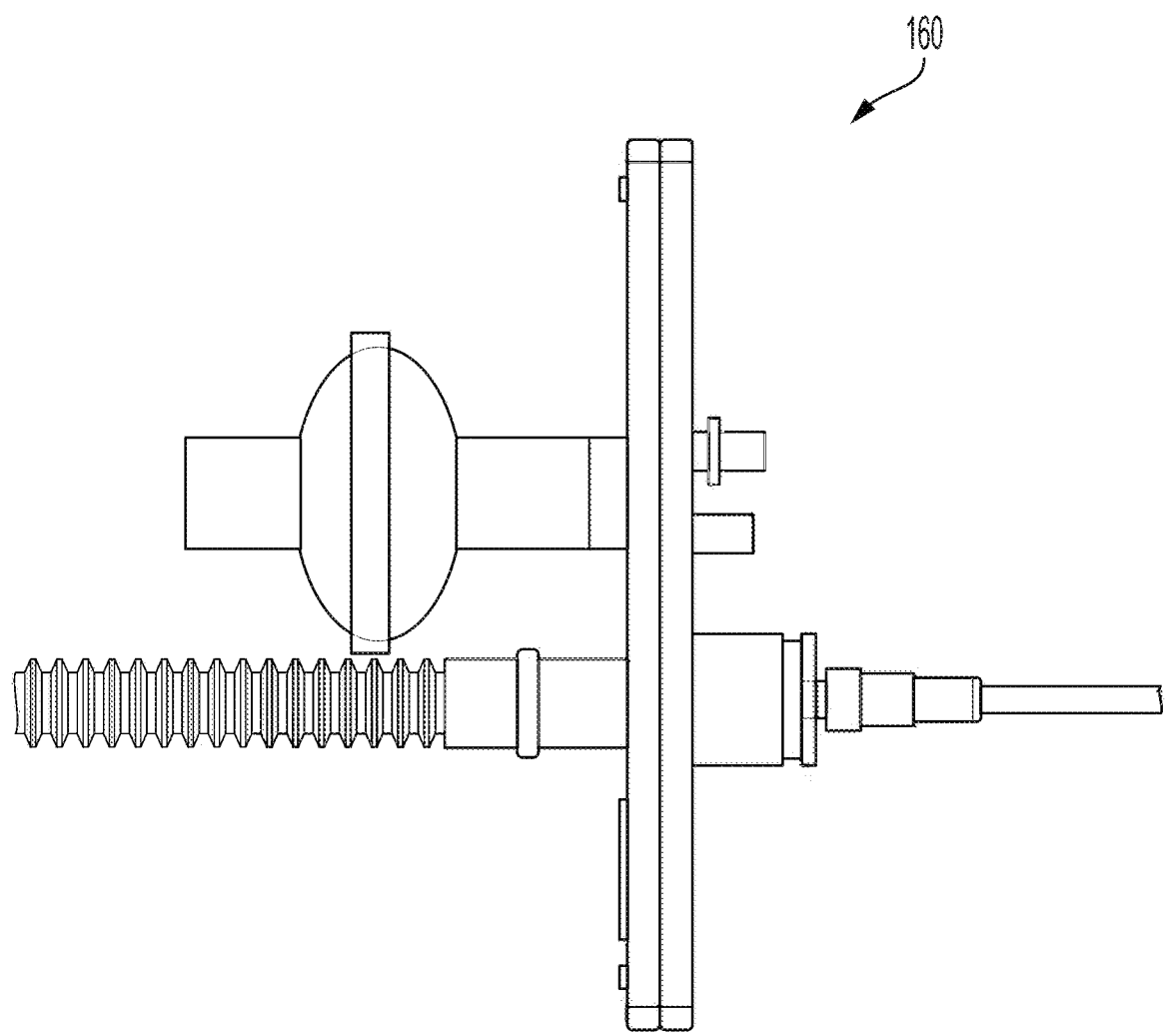
FIG. 12 is a side view of the respiratory and pressure manifold of FIG. 11.

With reference to FIGS. 11-12, the one or more manifolds 160 can support an oxygen supply and negative pressure channel 140. A manifold 160 can be disposed on a wall panel 112 (FIG. 10) such that it extends through wall panel 112 to provide oxygenation to the contained negative pressure environment NPAM device 50, including inflatable strut system 100. In some embodiments, a manifold 160 can be disposed below an access port 150 (FIG. 10) on a wall panel 112. Oxygen can be introduced while maintaining negative pressure in the contained environment. The practitioner or other personnel can actuate negative pressure channel 140 to suction air for maintaining negative pressure and preventing a positive pressure event, or relieving suction to prevent a high negative pressure event. In some embodiments, manifold 160 can include a baffling system for airflow direction into and/or out of the contained environment within NPAM device 50.

Although NPAM device 50 described herein is low risk, recirculation of air can present issues if an external suction device, for example, is improperly connected to negative pressure channel 140. Thus, the oxygen source can be applied to maintain proper oxygenation within inflatable strut system 100. In some embodiments, monitoring devices can be employed to track oxygen saturation. In some embodiments, a sensor to monitor end-tidal $CO_2$ (ETCO2) can also be provided. Accordingly, manifolds 160 can be employed to provide oxygenation to the contained negative pressure environment as a function of oxygen saturation and/or ETCO2. In this way, harmful conditions such as decreased oxygenation can be noted and oxygen level can be adjusted or inflatable strut system 100 can be removed. In some embodiments, manifold 160 can provide an indication (e.g., a light) that indicates whether the air pressure internal to NPAM device 50 is negative or positive. In some embodiments, manifold 160 can provide an indication (e.g., a light) that the patient within NPAM device 50 is under anesthesia.

Figure 13:
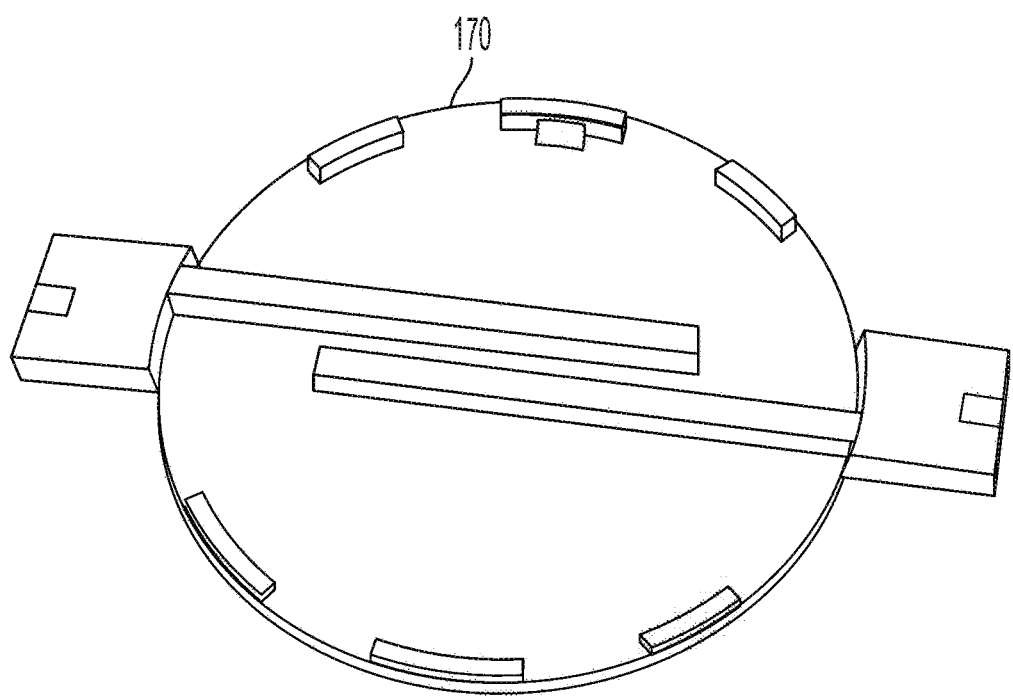
FIG. 13 is a perspective view of a negative pressure relief valve according to an embodiment.

As shown in FIG. 13, in some embodiments, a negative pressure relief valve 170 can be included in an NPAM device 50. In some embodiments, negative pressure relief valve 170 can be a one-way valve disposed on a wall panel 112 (FIG. 10). In some embodiments, a manifold 160 can be disposed below an access port 150 (FIG. 10) on a wall panel 112. In some embodiments, negative pressure relief valve can be positioned on a wall panel 112 that is opposite of a wall panel 112 on which manifold 160 (FIGS. 11-12) is positioned. The negative pressure maintained within main chamber 118 (FIG. 10) of NPAM device 50 can be approximately −2 Pa to approximately −125 Pa. Negative pressure relief valve 170 can provide ventilation to mitigate complications experienced by the patient from high negative pressure. For example, ventilation can be provided when air pressure within NPAM device 50 approaches or is less than approximately −125 Pa, such as approximately −124 Pa. In some embodiments, if the air pressure rises to a positive value such that the negative pressure environment is displaced, because negative pressure relief valve 170 is a one-way valve, air leakage and dispersion of contaminants to the ambient environment can be prevented.

As shown in FIG. 14, in some embodiments, a negative pressure flow gauge 180 can be included in an NPAM device 50. In some embodiments, negative pressure flow gauge 180 can be disposed on a wall panel 112 (FIG. 10). In some embodiments, negative pressure flow gauge 180 can be disposed below an access port 150 (FIG. 10) on a wall panel 112. In some embodiments, negative pressure flow gauge 180 can be disposed at an upper location on a wall panel 112 to be viewable by a practitioner or other personnel closer to their line of sight. In some embodiments, negative pressure flow gauge 180 can be attached on a swivel (not shown). Accordingly, the swivel can be maneuvered to face manifold 160 (FIGS. 11-12). In another example, the swivel can be rotated to maintain an upright position regardless of negative pressure flow gauge 180 regardless of the orientation on NPAM device 50. In some embodiments, negative pressure flow gauge 180 can be repositioned on NPAM device 50 (e.g., negative pressure flow gauge 180 can be removably attached via adhesive and/or multiple swivel attachments). In some embodiments, negative pressure flow gauge 180 can be positioned in-line with negative pressure channel 140 and/or negative pressure relief valve 170 or any other component.

Negative pressure flow gauge 180 can create motion in and/or levitate one or more balls (e.g. Styrofoam or other lightweight, consistent volume/density objects) that can act as floating bobbin flowmeters for main chamber 118 (FIG. 10). Accordingly, negative pressure flow gauge 180 can be used to monitor the air pressure internal to NPAM device 50 in which at least a portion of a patient may be positioned. In some embodiments, markings (e.g., lines, numbers, graphics, colors, strings, and/or grooves, etc.) (not shown) can be formed (e.g., printed, attached, and/or etched, etc.) onto NPAM device 50 (e.g., on one or more parts of frame 110) that can correspond to negative pressure flow gauge 180 and its pressure measurements. Negative pressure flow gauge 180 can include a bobbin supported by the air internal to NPAM device 50 and can reliably provide the pressure to within approximately 0.2 mm of its position. In this way, the position of a bobbin of negative pressure flow gauge can correspond to markings on NPAM device 50 to provide accurate and reliable pressure measurements.

By providing the practitioner or other personnel with pressure measurements, negative pressure flow gauge 180 can provide a safety mechanism in combination with negative pressure relief valve 170 (FIG. 13). Thus, negative pressure flow gauge 180 and/or negative pressure relief valve 170 can be additional safety mechanisms to alert (e.g., provide an indication) the practitioner and/or other personnel to high negative pressure events, which can cause complications for the patient. Negative pressure flow gauge 180 and/or negative pressure relief valve 170 can also alert (e.g., provide an indication) the practitioner and/or other personnel to positive pressure events, which can drive them to generate a negative pressure environment in NPAM device 50.

As shown in FIG. 15, in some embodiments, NPAM device 50 can be rigid strut system 1000 that can correspond to inflatable strut system 100 (FIGS. 1A-6) and/or inflatable strut system 200 (FIG. 6). One or more rigid struts 1160 can be disposed on rigid strut system 1000 to provide structure to wall panels 1120 and frame 1110. For example, a rigid strut 1160 can extend from a bottom to a top of a wall panel 1120. In some embodiments, rigid struts 1160 can be removably secured to attachment ports disposed on wall panels 1120. The attachment ports can include cavities that receive ends of rigid struts 1160. In some embodiments, rigid struts 1160 can be provided in hollow channels formed in wall panels 1120. Main chamber 1180 having an internal volume can be formed and maintained by deploying rigid strut system 1000. In some embodiments, wall panels 1120 and frame 1110 can be semi-rigid or rigid such that the rigid struts 1160 reinforce rigid strut system 1000.

In some embodiments, rigid strut system 1000 can be foldable. In some embodiments, rigid struts 1160 can be pliable or elastic rods that can be constrained when folded. In some embodiments, a rigid strut 1160 can include a joint to fold rigid strut 1160 when rigid strut system 1000 is folded. Accordingly, rigid struts 1160 can be at rest when folded. Rigid struts 1160 can be released during deployment of rigid strut system such that rigid struts 1160 pivot around their joints to extend. When extended, rigid struts 1160 provide structure to wall panels 1120 and frame 1110 and maintain the internal volume of main chamber 1180. Rigid strut system 1000 can be rapidly deployed by simultaneously pivoting all of the rigid struts 1160 around their joints to achieve their extended states, thereby rapidly deploying rigid strut system 1000.

With reference to FIGS. 16A-F, in some embodiments, NPAM device 50 can be tent system 2000. Tent system 2000 can be a protective cover to enclose a negative pressure environment and provide a single-patient enclosure. Tent system 2000 can be a foldable, portable, affordable, and lightweight embodiment that can be rapidly deployed (e.g., by unfolding, spreading, unraveling, stretching, and/or expanding tent system 2000), which is advantageous in triage and emergent critical care procedures, for example. Similar to inflatable strut system 100 and rigid strut system 1000, tent system 2000 can include one or more negative pressure channels 2400, one or more filters 2440, and/or one or more access ports 2500 that can correspond to those described above with respect to inflatable strut system 100. In addition, tent system 2000 can include an elastic band 2700, adhesive 2720, an invertible trash sack 2740, an attachment 2710, and/or a support structure 2730. In some embodiments, invertible trash sack 2740 can correspond to the waste receptacle described above with respect to inflatable strut system 100. Tent system 2000 can include any other components described herein with respect to alternative embodiments. Tent system 2000 can include a transparent or translucent plastic material (e.g., medical grade plastic, thermosets, thermoplastics such as vinyl, ABS, or HDPE, etc.).

In some embodiments, tent system 2000 can be draped to contain a volume in which to generate negative pressure. For example, in some embodiments, tent system 2000 can be draped over a structure and/or a patient and a negative pressure can be generated within the volume contained by tent system 2000. Accordingly, a patient can be contained within the negative pressure environment of tent system 2000. In some embodiments, support structure 2730 can be a holder for tent system 2000. In some embodiments, tent system 2000 can be suspended from support structure 2730 to create and maintain a volume in which to generate a negative pressure. Suspending tent system 2000 can also maintain a volume that extends from an overhead position to contain at least a portion of a patient, allow for movement within the volume, and prevent tent system 2000 from collapsing. In some embodiments, the volume created by suspension of tent system 2000 can provide sufficient room around the portion of the patient contained within the negative pressure environment. In some embodiments, support structure 2730 is an IV pole.

Attachment 2710 can be one or more fasteners (e.g., a zip tie, cord, plastic loop, hook, clip, ring, grommet, etc.) to secure an outer surface of tent system 2000 to support structure 2730. Attachment 2710 can be secured to the outer surface of tent system 2000, without creating an opening or rupturing tent system 2000. In some embodiments, a reinforcement panel can be included to prevent rupturing the protective cover when deploying tent system 2000. In some embodiments, the reinforcement panel in a proximal portion of tent system 100 (e.g., the portion to close at least a head and a portion of a chest of the patient) can correspond with a position of the chest of the patient. In some embodiments, the reinforcement panel can include a sterile cover that can be cut or removed.

In some embodiments, attachment 2710 can be included in a channel of tent system 2000. A resilient strip (not shown) can be contained in the channel and can move from a coiled position when tent system 2000 is folded to an extended position when tent system 2000 is unfolded. In this way, the resilient strip can form an internal frame of tent system 2000 to maintain a volume of the contained environment when the resilient strip is in the extended position.

Tent system 2000 can include adhesive 2720 on all sides and its perimeter to seal tent system 2000 to create and maintain an internal volume in which to generate a negative pressure. In some embodiments, a width of adhesive 2720 can be approximately 25.4 mm to approximately 50.8 mm. In some embodiments, tent system 2000 can include a drawstring as described above to at least partially close its perimeter. In some embodiments, tent system 2000 can include elastic band 2700, which can be cinched or tightened to at least partially secure and/or seal tent system 2000. In some embodiments, adhesive 2720, elastic band 2700, and/or a drawstring to seal tent system 2000 can be located at a distal portion of tent system 2000 (e.g., a perimeter of tent system 2000 or away from a head or a chest of the patient).

As shown in FIG. 17, in some embodiments, NPAM device 50 can be rigid box system 3000. Rigid box system 3000 can include drape 3220, one or more negative pressure channels 3400, and one or more access ports 3500. Negative pressure channels 3400 and access ports 3500 can correspond to those of inflatable strut system 100 described above. Drape 3220 can correspond to drape 120 of inflatable strut system 100 described above. Rigid box system 3000 can include can include any other components described herein with respect to alternative NPAM device 50 embodiments. Rigid box system 3000 can include a transparent or translucent plastic material, such as medical grade plastic.

Rigid box system 3000 can contain a volume in which a negative pressure can be generated. Because it is rigid, the volume can be maintained. Rigid box system 3000 can be placed over a portion of a patient's body to generate a contained negative pressure environment enclosing the portion of the patient's body. For example, a patient's head, neck, and/or torso can be received by rigid box system 3000. Drape 3220 can be sealed to rigid box system 3000 such that fluid communication between the volume internal to rigid box system 3000 and drape 3220 and the volume external to the components is prevented. Drape 3220 can extend from a lower end of rigid box system 3000 to enclose the environment and maintain a negative pressure. Drape 3220 can extend from rigid box system 3000 to a patient's feet, in an example. Accordingly, the patient can be contained within the negative pressure environment of rigid box system 3000 and drape 3220.

Rigid box system 3000 can be manufactured to various sizes depending on the application. For example, veterinary applications might require larger rigid box systems 3000 to accommodate a variety of veterinary patients. In some embodiments, rigid box system 3000 can be cleaned and reused.

As shown in FIG. 18, in some embodiments, NPAM device 50 can be wearable system 4000. Wearable system 4000 can include one or more negative pressure channels 4400, one or more elastic bands 4700, and/or a removable hood 4760. Negative pressure channels 4400 can correspond to negative pressure channels 140 of inflatable strut system 100 described above. Elastic bands 4700 can correspond to elastic band 2700 of tent system 2000 described above. Wearable system 4000 can be used with any other NPAM device 50 embodiments described herein and can include any other components described herein with respect to alternative NPAM device 50 embodiments. Wearable system 4000 can include a transparent or translucent plastic material (material (e.g., medical grade plastic, thermosets, thermoplastics such as vinyl, ABS, or HDPE, etc.).

In some embodiments, wearable system 4000 can be a hoodie (e.g., an aerosol mitigation hoodie) that can enclose at least a portion of a patient's body (e.g., the patient's shoulders, arms, chest, and torso). Removable hood 4760 can be the hood of wearable system 4000 and can be attached or detached via an airtight zipper. Negative pressure channels 4400 and other components, such as access ports, can be disposed on removable hood 4760. Wearable system 4000 can correspond to tent system 2000 described above, but instead of being draped to create and maintain an internal volume, wearable system 4000 is worn by a patient to maintain their enclosure in a negative pressure environment after exiting another NPAM device 50 (e.g., inflatable strut system 100, inflatable strut system 200, rigid strut system 1000, tent system 2000, or rigid box system 3000). In some embodiments, removable hood 4760 of wearable system 4000 can correspond to tent system 2000.

Wearable system 4000 can slip over the head of a patient and can be enclosed via elastic bands 4700 around the neck of a patient. Elastic band 4700 can be positioned at a convenient location with respect to the human body, e.g., toward a person's waist. Accordingly, elastic band 4700 can be drawn closed around the patient's waist or hips, for example, to create at least a partial seal. In some embodiments, elastic band 4700 can include a drawstring and/or adhesive.

Wearable system 4000 can be effective during procedures that produce aerosol, such as intubation, extubation, bronchoscopy, TEE, EGD, sinus surgery, etc. Similar to other NPAM device 50 embodiments, wearable system 4000 can be portable. An internal volume created around the head of the patient can support a negative pressure environment. A clearance around the patient's head can allow a practitioner to access the patient in the contained negative pressure environment. Wearable system 4000 is convenient for use with ambulatory patients, for example. As ambulatory patients are transferred from one location to another, the patients can utilize wearable system 4000 to continue being enclosed in a negative pressure environment to mitigate transmission risks. Further, during a pandemic, elective and some non-elective surgeries can be canceled due to limited resources and risk of possible contamination. Wearable system 4000 can be used for risk mitigation of pathogen transmission as low risk patients return to the operating room. Intubation/extubation can also be performed inside wearable system 4000. The patient can then recover in the post-anesthesia care unit (PACU) with a mask and wearable system 4000 applied for the duration of PACU stay. The use of wearable system 4000 can reduce risk of transmitting possible pathogens from the patient and allow for more rapid return of ambulatory surgery services.

Wearable system 4000 can also provide a rapid and portable way to produce a negative pressure environment enabling triage and emergent critical care procedures, and can allow for chest compressions. Additionally, by allowing EMS utilization in the field, wearable system 4000 can reduce or eliminate transmission to emergency and trauma teams in the field, ambulance, and hospital setting.

As shown in FIGS. 19A-C, in some embodiments, NPAM device 50 can be mask system 5000. Mask system 5000 can include one or more negative pressure channels 5400 one or access ports 5500, and/or one or more respiratory ports 5760. Negative pressure channels 5400, access ports 5500, and respiratory ports 5600 can correspond to negative pressure channels 140, access ports 150, and manifolds 160 of inflatable strut system 100 described above. Mask system can also include a strap 5770 and/or an ETCO2 monitor 5780. Mask system 5000 can be used with any other NPAM device 50 embodiments described herein and can include any other components described herein with respect to alternative NPAM device 50 embodiments.

Viral respiratory infections can be transmitted by aerosolization and droplet spread of an infected patient. An asymptomatic patient can still transmit the pathogen through coughing or during aerosolizing procedures. Before, during, and after procedures, for example, as ambulatory patients are transferred from one location to another, they can utilize mask system 5000 to continue being enclosed in a negative pressure environment to mitigate transmission risks. Pathogens can be contained using mask system 5000 and pathogen filtration can decrease aerosolization of pathogens localized at the face of the patient. Negative pressure channel 5400 can be included to provide suction and generate an internal negative pressure environment. Mask system 5000 can be a portable, disposable negative pressure system that covers only the nose/mouth area of a patient. Strap 5770 can be adjustable and can secure mask system 5000 close to the face of the patient to form a seal and prevent fluid communication between the contained negative pressure environment and the external environment. Respiratory port 5760 can deliver oxygen, and ETCO2 monitor 5780 can monitor for end-tidal CO2 (ETCO2). In some embodiments, mask system 5000 can have at least one access port 5500 for instrumentation. Access to the patient through mask system 5000 can be useful for certain less invasive airway procedures.

NPAM devices 50 described herein are affordable, portable, compact, disposable, and rapidly deployed solutions for mitigating aerosolization and droplet transmission to contain viral spread. Benefits also include remedying infrastructure and supply shortages experienced during high volume patient activity. Individual and localized negative pressure containment can reduce transmission risk and protect providers and other personnel in the vicinity of the patient to provide a safer environment during patient care for those proximate to the patient and/or the pathogen pathway.

The present invention(s) have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An aerosolization mitigation device, comprising: an inflatable strut system comprising: a front left strut and a front right strut; a rear left strut and a rear right strut; and a rear middle strut disposed between the rear left strut and the rear right strut; a transparent barrier configured to enclose a portion of a patient in a contained environment, the transparent barrier comprising a floor panel, wherein the transparent barrier is configured to form a volume around the patient when the inflatable strut system is in an inflated state, and wherein the front left strut, front right strut, rear left strut, right rear strut, and rear middle strut extend upward from the floor panel when the inflatable strut system is in the inflated state; a first top strut connected to upper ends of the front left strut and the front right strut; a window strut is connected from an upper end of the rear left strut, to the first top strut between the front left strut and front right strut, then to an upper end of the rear right strut, and then to an upper end of the rear middle strut; an opening between the front left strut and the right front strut configured to be sealed around the patient; a negative pressure channel configured to be coupled to a source of negative pressure, wherein the negative pressure channel is configured to generate a negative pressure in the volume around the patient in response to an application of the source of negative pressure; and an access port configured to provide a flow limited passageway through the transparent barrier into the volume around the patient when the inflatable strut system is in the inflated state.

2. The aerosolization mitigation device of claim 1, wherein the transparent barrier defines the opening and is formed as:
   a frame configured to enclose at least a head of the patient; and
   a drape configured to seal the opening around at least a portion of a neck of the patient,
   wherein the frame and the drape are sealed together at the opening such that fluid communication between the volume around the patient and an environment external to the transparent barrier is prevented.

3. The aerosolization mitigation device of claim 2, wherein the frame comprises a first material,
   wherein the drape comprises a second material different than the first material, and wherein the first material is less flexible than the second material.

4. The aerosolization mitigation device of claim 2, wherein a front edge of the drape further comprises a closing mechanism configured to close around the patient to maintain the negative pressure in the volume around the patient, and
wherein the closing mechanism comprises at least one of a string, adhesive, or elastic.

5. The aerosolization mitigation device of claim 1, wherein the transparent barrier further comprises a plurality of wall panels configured to seal with the inflatable strut system to prevent fluid communication between the volume around the patient and an environment external to the transparent barrier.

6. The aerosolization mitigation device of claim 5, wherein one of the plurality of wall panels on a side of the transparent barrier is configured to form an acute angle with a longitudinal axis generally perpendicular to a flat plane on which the aerosolization mitigation device is positioned in the inflated state.

7. The aerosolization mitigation device of claim 5, wherein a first wall panel is disposed between the rear left strut and the rear middle strut and a second wall panel is disposed between the rear right strut and the rear middle strut, and wherein the first and second wall panels are at an obtuse angle relative to each other in the inflated state.

8. The aerosolization mitigation device of claim 1, wherein the inflatable strut system comprises:
inflatable tubing forming a commonly inflatable volume; and
an inflation port, wherein the inflation port is fluidically coupled to the inflatable strut system.

9. The aerosolization mitigation device of claim 8, wherein the inflatable strut system further comprises a floor strut connected to lower ends of the front left strut and rear left strut and a second top strut connected to the upper end of the front left strut and an upper end of the rear left strut, wherein the front left strut, rear left strut, floor strut, and second top strut are configured to form a generally rectangular outline of a large and unobstructed view of the contained environment.

10. The aerosolization mitigation device of claim 1, wherein the opening further comprises a drape that extends outwardly from the transparent barrier.

11. The aerosolization mitigation device of claim 1, further comprising an attachment disposed on the transparent barrier to support at least one of a tool or an electronic device.

12. The aerosolization mitigation device of claim 1, further comprising a negative pressure relief valve disposed on the transparent barrier to provide an indication of a positive pressure event or a high negative pressure event in the volume around the patient.

13. The aerosolization mitigation device of claim 1, further comprising a negative pressure flow gauge corresponding to one or more markings formed on the transparent barrier.

14. An aerosolization mitigation device, comprising: an inflatable strut system comprising: a front left strut and a front right strut; a rear left strut and a rear right strut; a top strut connected to upper ends of the front left strut and front right strut; and a window strut is connected from an upper end of the rear left strut, to the top strut between the front left strut and front right strut, then to an upper end of the rear right strut, and then to an upper end of a rear middle strut; a transparent barrier configured to enclose a portion of a patient in a contained environment, the transparent barrier comprising a floor panel and a window panel, wherein the window panel is outlined by the window strut, wherein the transparent barrier is configured to form a volume around the patient when the inflatable strut system is in an inflated state, and wherein the front left strut, front right strut, rear left strut, and right rear strut, extend upward from the floor panel when the inflatable strut system is in the inflated state; an opening between the front left strut and the right front strut configured to be sealed around the patient; a negative pressure channel configured to be coupled to a source of negative pressure, wherein the negative pressure channel is configured to generate a negative pressure in the volume around the patient in response to an application of the source of negative pressure; and an access port configured to provide a flow limited passageway through the transparent barrier into the volume around the patient when the inflatable strut system is in the inflated state.

* * * * *